US012773538B2

(12) United States Patent
Hakim

(10) Patent No.: US 12,773,538 B2
(45) Date of Patent: Oct. 27, 2026

(54) SELF-ADJUSTING HYDROCEPHALUS VALVE

(71) Applicant: Carlos A. Hakim, Coconut Grove, FL (US)

(72) Inventor: Carlos A. Hakim, Coconut Grove, FL (US)

( * ) Notice: Subject to any disclaimer, the term of this patent is extended or adjusted under 35 U.S.C. 154(b) by 951 days.

(21) Appl. No.: 17/287,225

(22) PCT Filed: Oct. 24, 2019

(86) PCT No.: PCT/US2019/057862
§ 371 (c)(1),
(2) Date: Apr. 21, 2021

(87) PCT Pub. No.: WO2020/086847
PCT Pub. Date: Apr. 30, 2020

(65) Prior Publication Data

US 2021/0379344 A1 Dec. 9, 2021

Related U.S. Application Data

(60) Provisional application No. 62/750,897, filed on Oct. 26, 2018.

(51) Int. Cl.
*A61M 27/00* (2006.01)
*A61M 39/02* (2006.01)
*A61M 39/24* (2006.01)

(52) U.S. Cl.
CPC ...... *A61M 27/006* (2013.01); *A61M 39/0247* (2013.01); *A61M 39/24* (2013.01);
(Continued)

(58) Field of Classification Search
CPC ............ A61M 27/006; A61M 39/0247; A61M 39/24; A61M 2039/025; A61M 2039/027;
(Continued)

(56) References Cited

U.S. PATENT DOCUMENTS 3,886,948 A 6/1975 Hakim
3,924,635 A 12/1975 Hakim
(Continued)

FOREIGN PATENT DOCUMENTS

EP 2008683 A1 12/2008
EP 2314214 A2 4/2011
(Continued)

OTHER PUBLICATIONS

International Search Report and Written Opinion in International Patent Application No. PCT/US2019/057862 dated Mar. 3, 2020.
(Continued)

*Primary Examiner* — Philip R Wiest
*Assistant Examiner* — Hans Kaliher
(74) *Attorney, Agent, or Firm* — Lando & Anastasi, LLP

(57) ABSTRACT

A system and method of accurately measuring a pressure (Pp) within a human brain using totally-implanted or partially-external hardware. The system includes a first pressure transducer configured to measure a cerebrospinal fluid pressure (Pcsf) within a ventricle of a brain, a second pressure transducer configured to indirectly measure a second pressure (Pp) within a space of the brain, and an adjustable implanted valve controller configured to calculate the effective differential pressure (Pei=Pcsf−Pp) between the measured pressures Pcsf and the Pp and determine whether the effective differential pressure measurement represents a true secondary pressure.

21 Claims, 14 Drawing Sheets

(52) U.S. Cl.
CPC . *A61M 2039/025* (2013.01); *A61M 2039/027* (2013.01); *A61M 2039/0276* (2013.01); *A61M 2039/242* (2013.01); *A61M 2205/18* (2013.01); *A61M 2205/3344* (2013.01); *A61M 2205/3576* (2013.01); *A61M 2205/52* (2013.01); *A61M 2205/581* (2013.01); *A61M 2205/583* (2013.01); *A61M 2205/8206* (2013.01); *A61M 2210/0693* (2013.01); *A61M 2230/005* (2013.01)

(58) Field of Classification Search
CPC .... A61M 2039/0276; A61M 2039/242; A61M 2205/18; A61M 2205/3344; A61M 2205/3576; A61M 2205/52; A61M 2205/581; A61M 2205/8206; A61M 2210/0693; A61M 2230/005
See application file for complete search history.

(56) References Cited

U.S. PATENT DOCUMENTS

| | | | | |
|---|---|---|---|---|
| 4,106,510 | A | 8/1978 | Hakim et al. | |
| 4,787,886 | A | 11/1988 | Cosman | |
| 8,679,048 | B2 * | 3/2014 | Sundstrom | A61B 5/031 604/9 |
| 2004/0068221 | A1 * | 4/2004 | Silverberg | A61M 27/006 604/9 |
| 2007/0112291 | A1 | 5/2007 | Borgesen | |
| 2008/0125690 | A1 * | 5/2008 | Delaporte | A61M 27/006 604/9 |
| 2009/0005720 | A1 * | 1/2009 | Ludin | A61M 27/006 604/9 |
| 2010/0256549 | A1 | 10/2010 | Kralick et al. | |
| 2011/0092846 | A1 | 4/2011 | Kassem | |
| 2013/0197422 | A1 * | 8/2013 | Browd | A61B 5/031 604/9 |
| 2014/0243703 | A1 | 8/2014 | Schmidt et al. | |
| 2014/0275830 | A1 | 9/2014 | Osorio et al. | |
| 2016/0136398 | A1 | 5/2016 | Heilman et al. | |
| 2016/0331949 | A1 * | 11/2016 | Lutz | A61M 27/006 |
| 2017/0203083 | A1 * | 7/2017 | Chappel | A61M 27/006 |
| 2017/0354337 | A1 | 12/2017 | Schmidt et al. | |
| 2018/0228970 | A1 | 8/2018 | Wostyn | |

FOREIGN PATENT DOCUMENTS

| | | | |
|---|---|---|---|
| JP | 2004-508109 | A | 3/2004 |
| JP | 2005-13727 | A | 1/2005 |
| JP | 2011-87932 | A | 5/2011 |
| JP | 2014-514027 | A | 6/2014 |
| KR | 10-2017-0132835 | A | 12/2017 |
| WO | 2016/160463 | A1 | 10/2016 |

OTHER PUBLICATIONS

Extended European Search Report in corresponding European Patent Application No. 19874937.6 dated Jun. 22, 2022.

Office Action for CA Application No. 3,117,659 dated Dec. 15, 2025.

Freimann, F.B., et al., “Feasibility of Telemetric ICP-Guided Valve Adjustments for Complex Shunt Therapy,” Childs Nerv. Syst., 30: 689-697 (2014).

* cited by examiner

SELF-ADJUSTING HYDROCEPHALUS VALVE

RELATED APPLICATIONS

This application is a U.S. National Stage Application under 35 U.S.C. § 371 of International Application No. PCT/US2019/057862, filed Oct. 24, 2019, which claims benefit of U.S. Provisional Application No. 62/750,897, filed Oct. 26, 2018, the contents of which are incorporated herein by reference in their entirety.

BACKGROUND

Hydrocephalus is a condition associated with ventricular volume enlargement caused by net accumulation of cerebrospinal fluid (CSF) in the ventricles of the brain. Non-communicating hydrocephalus (obstructive) or High Pressure Hydrocephalus (HPH) is hydrocephalus associated with an obstruction in the ventricular system or CSF flow pathways, and is generally characterized by increased cerebrospinal fluid (CSF) pressure. HPH also results when there is no obstruction in the ventricular flow pathways, but the obstruction occurs where CSF drains out of the ventricular system into the bloodstream. In contrast, a communicating (or non-obstructive) form of hydrocephalus, which does not arise from a visible (i.e., identifiable) blockage in the flow of cerebrospinal fluid, may also occur. Normal Pressure Hydrocephalus (NPH), one form of communicating hydrocephalus where there is ventricular volume enlargement at virtually normal CSF pressure, is a clinical condition which principally affects the elderly. In this type of hydrocephalus, the CSF pathways are intact and the drainage into the bloodstream is unimpaired. NPH is characterized by three symptoms known as the Hakim triad associated with ventricular volume enlargement in the absence of elevated intracranial pressure:

- Motor disturbances (mostly gait impairment) are usually the first to occur;
- incontinence (primarily urinary), and
- dementia.

Depending on the severity and degree of progression, one, two or all three symptoms may be present, with gait impairment typically being the presenting symptom. In summary, NPH presents as an enlargement of the ventricles under conditions of normal CSF pressure.

NPH is a known and unique clinical condition justifying its own differential diagnosis with other brain atrophies and dementias. Unlike most dementias, the dementia associated with NPH is reversible with treatment by implantation of a shunt.

The objective in the treatment of all forms of hydrocephalus is to reduce the ventricular volume by reducing ventricular pressure so that ventricular volume normalizes. Both types of hydrocephalus, HPH and NPH, are often treated by implanting into the brain's fluid compartment, a shunt that drains excess CSF from the ventricles or from the lumbar thecal space (which communicates with the brain's fluid compartment in communicating hydrocephalus). Examples of such shunts include:

- ventriculoatrial (VA) shunts that divert fluid from the cerebral ventricles to the right atrium of the heart,
- ventriculoperitoneal (VP) shunts that divert fluid from the cerebral ventricles to the peritoneum, and
- lumboperitoneal (LP) shunts that divert CSF from the lumbar region to the peritoneum.

Ventricular shunts may be used in patients with communicating or non-communicating hydrocephalus, but lumbar shunts may only be implanted in patients with communicating hydrocephalus.

These shunts are generally comprised of:

- an inflow catheter such as a cerebral catheter (for ventricular shunts) inserted through the brain parenchyma into the ventricle or a lumbar catheter (for lumbar shunts) inserted through a hollow needle into the lumbar thecal space,
- a one-way valve system that controls the pressure of fluid from either the cerebral ventricles or the lumbar region, and
- an outflow catheter inserted into a reservoir of the body, such as the jugular vein (with the tip advanced to the right atrium of the heart) or the peritoneal cavity, from which the CSF is absorbed thus bypassing the obstruction in non-communicating or obstructive hydrocephalus and lowering the CSF pressure below the parenchymal pressure (and normalizing ventricular volume) in NPH.

Ventriculoatrial, ventriculoperitoneal and lumboperitoneal shunts are available with valve mechanisms that are either fixed- or variable-pressure (programmable or adjustable), as discussed further below.

Additionally, as a temporary procedure prior to the permanent implant of a shunt, an external drainage system (EDS) draining from the ventricle to a drainage bag (external ventricular drainage system or EVDS) or from the lumbar thecal space to a drainage bag (external lumbar drainage system or ELDS) may be used for several weeks for management of intracranial pressure (ICP) or to manage conditions including, but not limited to, infection, intraventricular hemorrhage, elevated CSF proteins, etc. or as a screening procedure for NPH to determine whether an implantable shunt is a management option.

SUMMARY OF INVENTION

There is a need in the art for self-adjusting hydrocephalus valves (implantable and external) for the treatment of hydrocephalus and related disorders of the cerebrospinal fluid (CSF) spaces to optimize shunting for the specific condition(s) being treated because the current art provides technology that, at best, may be adjusted only during periodic visits to the clinician. Accordingly, aspects and embodiments are directed to a self-adjusting valve and methods of operation of the same that allow the valve to automatically adjust whenever and wherever the patient's requirements change.

According to one embodiment, a method of accurately measuring the secondary, e.g., intraparenchymal venous, pressure (Pp), within the human brain using totally-implanted or partially-external hardware comprises measuring the cerebral spinal fluid pressure (Pcsf) within the ventricle of a brain, indirectly measuring the intraparenchymal pressure (Pp) within the parenchyma space of the brain, calculating the effective differential pressure ($P_{ei}=P_{csf}-P_p$) between the measured pressures Pcsf and the Pp, and determining whether the effective differential pressure measurement represents the true intraparenchymal pressure.

In one example if the cerebral spinal fluid pressure measurement (Pcsf) of the ventricle is equal to or within a specified differential pressure threshold to the intraparenchymal pressure (Pp) of the parenchymal space of the brain, the pressure of the ventricle of the brain is reduced by a predetermined pressure value. In one example the specified pressure reduction is 10 mmH2O. The method may further comprise continuing to reduce the pressure within the ventricles of the brain until the Pcsf pressure measurement is lower than the Pp pressure measurement by the specified differential pressure threshold. In one example the specified differential pressure threshold is 20 mmH2O. In another example the Pp measurement represents the true intraparenchymal venous pressure.

In certain examples of the method the reduction of the cerebrospinal fluid pressure treats High Pressure Hydrocephalus.

In certain examples of the method the reduction of the cerebral spinal fluid pressure treats Normal Pressure Hydrocephalus.

In certain examples of the method the reduction of the cerebrospinal fluid pressure treats the condition of Pseudotumor cerebri (Idiopathic Intracranial Hypertension).

In certain examples of the method continued measurements of Pcsf and Pp provides a steady state balance of ventricular volume and the intraparenchymal venous pressure.

According to another embodiment a surgically-implantable shunt valve system comprises an inflow catheter that is implanted in the ventricle of the brain or the CSF space in the spinal column connected to an inlet port, a shunt valve assembly configured such that an aperture of the shunt valve assembly opens when a pressure of the fluid in the inlet port exceeds a selected pressure setting of the shunt valve assembly so as to vent fluid through the aperture into an outlet port, an outflow catheter which provides drainage of fluid from the outlet port to a cavity within the human body where cerebrospinal fluid may be absorbed, a first pressure transducer attached to the inflow catheter for the measurement of cerebrospinal fluid pressure, a second pressure transducer attached to the inflow catheter for the measurement of intraparenchymal pressure, and an adjustable implanted valve controller configured to change the valve pressure setting based on measurements from the pressure transducers.

According to another embodiment a partially-implanted and partially-external implantable shunt valve system comprises an implanted inflow catheter that is surgically placed in the ventricle of the brain or the CSF space in the spinal column connected to an inlet port, an external shunt valve assembly configured such that an aperture of the shunt valve assembly opens when a pressure of the fluid in the inlet port exceeds a selected pressure setting of the shunt valve assembly so as to vent fluid through the aperture into an outlet port, an external outflow tube connected to an external drainage bag which provides drainage of fluid from the outlet port to the bag external to the human body where cerebrospinal fluid may be collected for analysis and/or disposal, a first pressure transducer attached to the inflow catheter for the measurement of cerebrospinal fluid pressure, a second pressure transducer attached to the inflow catheter for the measurement of intraparenchymal pressure, an adjustable valve controller configured to change the valve pressure setting based on measurements from the pressure transducers, and an external screen display that displays the direct measured CSF and intraparenchymal pressure measurements in clinically useful values of mmH2O, mmHg, etc. as instantaneous and trended values and other secondary measurements that provide information useful to the clinician.

In certain examples the first pressure transducer for measurement of cerebrospinal fluid pressure (Pcsf) provides a first electrical signal representing the measured pressure to the valve controller.

In certain examples the second pressure transducer for measurement of intraparenchymal pressure (Pp) provides a second electrical signal representing the measured pressure to the valve controller.

In one example the valve controller calculates the pressure difference between the measured Pcsf and Pp pressures. The valve controller may determine whether the pressure differential between the Pcsf and Pp has exceeded a predetermined level. In one example if the valve controller determines that the pressure differential between the Pcsf and Pp is less than a predetermined level, then the valve controller reduces the pressure setting of the shunt valve assembly by a predetermined value. In one example the predetermined pressure level is 10 mmH2O. In another example if the valve controller determines that the pressure differential between the Pcsf and Pp is greater than a predetermined level, then the valve controller identifies the measured Pp pressure as the true Pp pressure.

According to another embodiment a surgically-implantable shunt valve system comprises an inflow catheter that is implanted in a ventricle of the brain or the CSF space in the spinal column connected to an inlet port, a shunt valve assembly configured such that an aperture of the shunt valve assembly opens when a pressure of the fluid in the inlet port exceeds a selected pressure setting of the shunt valve assembly so as to vent fluid through the aperture into an outlet port, an outflow catheter which provides drainage of fluid from the outlet port to a cavity within the body, and a first pressure transducer attached to the inflow catheter for measurement of intraparenchymal pressure (Pp), a second pressure transducer attached to the inflow catheter for measurement of cerebrospinal fluid pressure (Pcsf), and an adjustable implanted valve controller configured to determine whether there is a condition of High Pressure Hydrocephalus (HPH), Normal Pressure Hydrocephalus (NPH), or Pseudo Tumor in the brain based on the Pcsf and/or Pp measurements as compared to a predetermined threshold value.

In one example the first pressure transducer for measurement of intraparenchymal pressure (Pp) provides an electrical signal representing the measured pressure to the valve controller each time the Pcsf is measured.

In one example the valve controller reduces the pressure setting of the surgically-implantable shunt valve assembly by a predetermined value. In another example the valve controller determines whether the measured Pcsf pressure is less than the measured Pp pressure by a pressure value greater than a predetermined amount. In one example the difference between the Pp and Pcsf is greater than 20 mmH2O. In another example the valve controller maintains the valve pressure setting until the volume of the brain's ventricles is reduced to a normal volume. In another example the valve controller increases the pressure setting of the valve assembly until the Pcsf is equal to the Pp.

According to another embodiment, a surgically-implantable shunt valve system comprises an inflow catheter that is implanted in the ventricle of the brain or the CSF space in the spinal column connected to an inlet port, a shunt valve assembly configured such that an aperture of the shunt valve assembly opens when a pressure of the fluid in the inlet port exceeds a selected pressure setting of the shunt valve assembly so as to vent fluid through the aperture into an outlet port, an outflow catheter which provides drainage of fluid from the outlet port to a cavity within the human body, a first pressure transducer attached to the inflow catheter for measurement of cerebrospinal fluid pressure, a second pressure transducer attached to the inflow catheter for measurement of intraparenchymal pressure, an adjustable implanted valve controller configured to change the valve pressure settings based on measurements from the first and second pressure transducers, an implantable power source, and a wireless communications mechanism between the adjustable implanted valve controller and an external programming instrument.

In one example the shunt valve assembly includes an implanted adjustable valve separate from the adjustable implanted valve controller. In another example the implanted adjustable valve is electrically interfaced to the valve controller with a valve communications cable. In another example the programmer wirelessly receives operational settings and data from the valve controller. In another example the programmer wirelessly transmits new values of operational settings to the valve controller.

In one example the shunt valve assembly includes an implanted adjustable valve that is an integrated module within the valve controller. In one example the adjustable valve is located within a polymer header of the implanted valve controller. In another example the inflow catheter from the ventricle includes wires for transmitting the pressure values from the first and second pressure transducers to the implanted valve controller. In one example the integrated adjustable valve and valve controller are a separate implanted device from the implanted power source and the wireless communications mechanism. In one example the shunt valve system further comprises an electrical cable connected between the integrated adjustable valve and valve controller and the implanted power source and the wireless communications mechanism. In one example the implanted power source is a primary battery. In another example the implanted power source is a rechargeable battery. In one example the implanted rechargeable battery is recharged through wireless means from an external instrument. In one example the implanted valve controller and adjustable valve are located proximal to the skull of a human patient. In another example the implanted valve controller and adjustable valve receive continuous power wirelessly from a portable external instrument.

Another embodiment is directed to a method of operating a surgically-implantable shunt valve assembly with pressure sensors configured to be implantable in fluid communication with the ventricle of the brain, providing pressure data to a valve controller. In one embodiment the method comprises measuring the cerebrospinal fluid pressure (Pcsf) within the ventricle of a brain, measuring the intraparenchymal pressure (Pp) within the parenchyma space of the brain, calculating the differential pressure between the measured pressures Pcsf and the Pp, and determining whether to adjust the pressure setting of a shunt valve of the surgically-implantable shunt valve assembly based on the differential pressure.

In one example the Pcsf being greater than a predetermined threshold is indicative of High Pressure Hydrocephalus. In one example the predetermined threshold is 220 mmH2O.

The method may further comprise reducing the pressure setting of the shunt valve by a predetermined decrement using the valve controller. In one example the predetermined decrement is 10 mmH2O.

The method may further comprise determining whether the differential pressure between Pp and Pcsf is greater than a predetermined differential pressure threshold. In one example the predetermined differential pressure threshold is 10 mmH2O. The method may further comprise continuing to reduce the shunt valve pressure setting using the valve controller until the differential pressure between Pp and Pcsf is greater than a second predetermined differential pressure threshold. In one example the second predetermined differential pressure threshold is 20 mmH2O. In one example the method further comprises maintaining the pressure setting using the valve controller until the ventricles return to normal size or volume. In another example the method further comprises increases the pressure setting of the shunt valve using the valve controller until Pp and Pcsf are equal. In one example the method further comprises recording the Pp and Pcsf values in memory using the valve controller. In one example the patient is clinically diagnosed with Normal Pressure Hydrocephalus with a normal Pcsf measurement. In one example the Pcsf measurement is 150 mmH2O. The method may further comprise using the valve controller to reduce the pressure setting of the shunt valve by a predetermined decrement. In one example the predetermined decrement is 10 mmH2O. The method may further comprise using the valve controller to determine whether the differential pressure between Pp and Pcsf is greater than a predetermined threshold. In one example the predetermined differential pressure threshold is 10 mmH2O. The method may further comprise using the valve controller to continue to reduce the shunt valve pressure setting until the differential pressure between Pp and Pcsf is greater than a second predetermined threshold. In one example the second predetermined differential pressure threshold is 20 mmH2O. The method may further comprise maintaining the pressure setting using the valve controller until the ventricles return to normal size or volume. In one example the method further comprises increasing the pressure setting of the shunt valve using the valve controller until Pp and Pcsf are equal. The method may further comprise recording the Pp and Pcsf values in memory using the valve controller.

According to another embodiment a surgically-implantable shunt valve system comprises an inflow catheter that is implanted in the ventricle of the brain or the CSF space in the spinal column connected to an inlet port, a shunt valve assembly including a shunt valve and configured such that an aperture of the shunt valve opens when a pressure of the fluid in the inlet port exceeds a selected pressure setting of the shunt valve assembly so as to vent fluid through the aperture into an outlet port, an outflow catheter which provides drainage of fluid from the outlet port to a cavity within the human body, a first pressure transducer attached to the inflow catheter for measurement of cerebrospinal fluid pressure, a second pressure transducer attached to the inflow catheter for measurement of intraparenchymal pressure, an adjustable implanted valve controller configured to change the valve pressure settings based on measurements from the first and second pressure transducers, an implantable power source, a first wireless communications device configured to provide wireless communications between the external programming instrument and the implanted valve controller, and a second wireless communications device configured to provide wireless communications between the implanted valve controller and an external patient receiver.

In one example the implanted valve controller provides wireless data transfer to the external patient receiver. In one example the data to be transferred includes measured pressure signals from the first and second pressure transducers. In another example the data to be transferred includes alarm data. The alarm data may be indicative of abnormal pressure measurements obtained from the first and second pressure transducers. In one example the alarm data is indicative of a device system fault. In one example the external patient receiver provides an audio alarm to the patient. In another example the external patient receiver provides a visual alarm to the patient. In certain examples the valve controller wirelessly transfers all measured data to the external patient receiver after an alarm signal is transferred.

According to another embodiment a shunt valve system comprises an inflow catheter that is implanted in the ventricle of the brain or the CSF space in the spinal column connected to an inlet port, a shunt valve assembly configured such that an aperture of the shunt valve assembly opens when a pressure of the fluid in the inlet port exceeds a selected pressure setting of the shunt valve assembly so as to vent fluid through the aperture into an outlet port, an outflow catheter which provides drainage of fluid from the outlet port to an external ventricular drainage system, a first pressure transducer attached to the inflow catheter for the measurement of cerebrospinal fluid pressure, a second pressure transducer attached to the inflow catheter for the measurement of intraparenchymal pressure, and an adjustable valve controller configured to change the valve pressure setting based on measurements from the pressure transducers.

In one example the first pressure transducer for measurement of cerebrospinal fluid pressure (Pcsf) provides a first electrical signal representing the measured pressure to the valve controller. In another example the second pressure transducer for measurement of intraparenchymal pressure (Pp) provides a second electrical signal representing the measured pressure to the valve controller. In one example the valve controller calculates the pressure difference between the measured Pcsf and Pp pressures. In another example the valve controller determines whether the pressure differential between the Pcsf and Pp has exceeded a predetermined level. In one example if the valve controller determines that the pressure differential between the Pcsf and Pp is less than a predetermined level, then the valve controller reduces the pressure setting of the shunt valve assembly by a predetermined value. In one example the predetermined pressure level is 10 mmH2O. In another example if the valve controller determines that the pressure differential between the Pcsf and Pp is greater than a predetermined level, then the valve controller identifies the measured Pp pressure as the true Pp pressure.

According to another embodiment a shunt valve system comprises an inflow catheter that is implanted in the ventricle of the brain or the CSF space in the spinal column connected to an inlet port, a shunt valve assembly configured such that an aperture of the shunt valve assembly opens when a pressure of the fluid in the inlet port exceeds a selected pressure setting of the shunt valve assembly so as to vent fluid through the aperture into an outlet port, an outflow catheter which provides drainage of fluid from the outlet port to a cavity within the human body where cerebrospinal fluid may be absorbed, a differential pressure transducer attached to the inflow catheter and configured to measure cerebrospinal fluid pressure (Pcsf) and intraparenchymal pressure (Pp), and an adjustable valve controller configured to calculate the pressure difference between the measured cerebrospinal fluid pressure and intraparenchymal pressure and to change the valve pressure setting based on the measurements from the differential pressure transducer.

In one example the differential pressure transducer includes a first pressure transducer for measurement of the cerebrospinal fluid pressure and a second pressure transducer for measurement of the intraparenchymal pressure.

In one example the valve controller is further configured to determine whether the pressure differential between the Pcsf and Pp has exceeded a predetermined level. In one example if the valve controller determines that the pressure differential between the Pcsf and Pp is less than a predetermined level, then the valve controller reduces the pressure setting of the shunt valve assembly by a predetermined value. The predetermined pressure level may be 10 mmH2O, for example. In another example if the valve controller determines that the pressure differential between the Pcsf and Pp is greater than a predetermined level, then the valve controller identifies the measured Pp pressure as the true Pp pressure.

Another embodiment is directed to a method of operating a shunt valve assembly with pressure sensors configured to be in fluid communication with the ventricle of the brain, providing pressure data to a valve controller. In one embodiment the method comprises measuring the cerebrospinal fluid pressure (Pcsf) within the ventricle of a brain, measuring the intraparenchymal pressure (Pp) within the parenchyma space of the brain, calculating the differential pressure between the measured pressures Pcsf and the Pp, and determining whether to adjust the pressure setting of a shunt valve of the shunt valve assembly based on the differential pressure.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of embodiments are discussed below regarding the accompanying drawings. For purposes of clarity, not every component may be labeled in every drawing. The drawings are not necessarily to scale; emphasis instead being placed upon illustrating the principles of the invention. The drawings are included to provide illustration and a further understanding of the various aspects and embodiments and are incorporated in and constitute a part of this specification, but are not intended as a definition of the limits of the invention. In the drawings.

DETAILED DESCRIPTION

Figure 1:
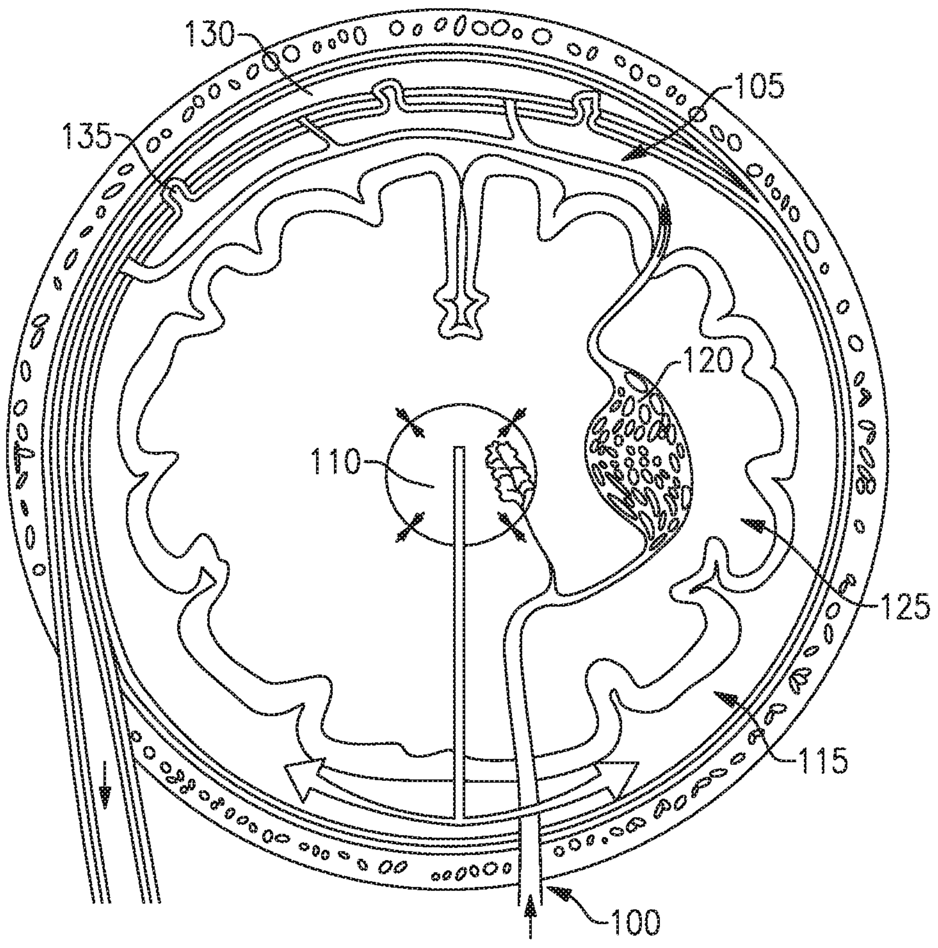
FIG. 1 is a diagram showing the anatomical structure of the human brain, presented in a spherical model, with references to various structures and associated pressure measurements.

Aspects and embodiments are directed to a self-adjusting valve that is configured to be implanted into a patient, or connected to a catheter implanted into a patient, and used to regulate the flow (drainage) of cerebrospinal fluid (CSF).

Definitions

Arachnoid Villi: Microscopic projections of the arachnoid into some of the venous sinuses through which CSF drains into the bloodstream.

Atrium: One of two upper chambers in which blood enters the heart.

Catheter: A thin tube made from medical grade materials for fluid diversion.

Catheter, Atrial Distal outflow tube of a shunt draining into the atrium.

Catheter, Drainage: Distal outflow catheter (tube) of a shunt; a tube from which fluid exits a shunt valve system.

Catheter, Inflow: Proximal tube of a shunt placed in one of the cerebrospinal fluid compartments through which CSF flows into a shunt valve system.

Catheter, Lumbar: Proximal tube of a shunt through which CSF is drained from the CSF spaces around the spine.

Catheter, Peritoneal: Distal outflow tube of a shunt draining into the peritoneum.

Catheter, Ventricular: Proximal inflow tube of a shunt draining CSF from the ventricles of the brain.

Cerebrospinal Fluid: Clear, colorless body fluid bathing the brain and spinal cord produced primarily in the choroid plexuses of the ventricles of the brain. Acting as a cushion or buffer for the brain and providing basic mechanical and immunological protection to the brain within the skull and vertebral column.

Choroid Plexus: Choroid plexus is a plexus of cells that produces the majority of cerebrospinal fluid in the ventricles of the brain. The choroid plexus consists of modified ependymal cells.

External Drainage System (EDS) External drainage and monitoring is the temporary CSF drainage from the brain's lateral ventricles, or the lumbar space of the spine, into an external collection bag by using a combination of gravity and CSF pressure.

External Lumbar Drainage System (ELDS) External drainage and monitoring is the temporary CSF drainage from the lumbar space of the spine into an external collection bag by using a combination of gravity and CSF pressure.

External Ventricular Drainage System (EVDS) External drainage and monitoring is the temporary CSF drainage from the brain's lateral ventricles into an external collection bag by using a combination of gravity and CSF pressure.

Fixed pressure Hydrocephalus: A valve that operates at a single operating pressure. Condition associated with ventricular volume enlargement caused by net accumulation of cerebrospinal fluid (CSF) in the ventricles of the brain.

Hydrocephalus, Communicating: Non-obstructive hydrocephalus; a form of hydrocephalus, which does not arise from a visible blockage in the flow of CSF.

Hydrocephalus, High Pressure: Hypertensive hydrocephalus; a neurological disorder in which there is excessive accumulation of CSF within the ventricles of the brain. CSF accumulates resulting in increased pressure inside the brain (skull) causing the ventricular volume to enlarge and the brain tissue to stretch exerting pressure on critical structures.

Hydrocephalus, Non-obstructive: See communicating hydrocephalus.

Hydrocephalus, Normal Pressure: Abbreviated NPH, this condition is an accumulation of CSF that causes the ventricles in the brain to become enlarged, sometimes with little or no increase in ICP, in which a triad (a group of three) of neurologic symptoms occurs in the presence of "normal" CSF pressure-gait disturbances (typically first to present), dementia, and impaired bladder control. Depending on severity, one or more of these symptoms present.

Hydrocephalus, Obstructive: See high-pressure hydrocephalus.

Lumboperitoneal shunt: A shunt-valve system to divert CSF from the subarachnoid (lumbar thecal) space in the lower back to the abdominal cavity.

Parenchyma, Brain: Functional tissue in the brain made up of the two types of brain cell, neurons and glial cells.

Peritoneum: The serous membrane lining the cavity of the abdomen and covering the abdominal organs.

Pressure, Subarachnoid: CSF pressure measured in the subarachnoid CSF space.

Pressure, Subdural: Pressure measured in the subdural space.

Programmable pressure: A variable-pressure valve mechanism with a noninvasively-adjustable range of operating pressures changeable by means of a programmer.

Shunt: An implanted device that typically includes two catheters (in-flow and out-flow) and a one-way valve which regulates the amount, flow direction, and pressure of CSF of the brain's fluid compartments.

Sinus, Superior Sagittal: The superior, longitudinal sinus within the human skull; an unpaired area along the attached margin of the falx cerebri that allows blood to drain from the lateral aspects of anterior cerebral hemispheres to the confluence of sinuses.

Space, Lumbar Thecal: The CSF fluid compartment surrounded by the thecal or dural sac; the membranous sheath of dura mater that surrounds the spinal cord and the cauda equina. The thecal sac contains the cerebrospinal fluid in which the spinal cord "floats".

Space, Subarachnoid: The interval between the arachnoid membrane and the pia mater, occupied by delicate connective tissue trabeculae and intercommunicating channels containing CSF.

Valve: A resistance regulating mechanism in a shunt, which allows fluid flow in only one direction. Classically, valves may be fixed pressure or noninvasively adjustable pressure.

Vein, Jugular: The veins in the neck that carry blood from the head to the superior vena cava (the main vein of the upper body), which empty into the heart.

Vein(s), Superficial Cerebral: A group of cerebral veins in the head including the superior cerebral veins, the superficial middle cerebral vein, the inferior cerebral veins, the inferior anastomotic vein and the superior anastomotic vein.

Ventricle(s): Ependymal-cell lined cavities in the brain in which CSF is produced and afterwards circulated around the cranial cavity which communicate with the spinal subarachnoid space(s) or drain into the arachnoid villi. The ventricles include paired lateral ventricles which drain into the third and, subsequently, the fourth ventricle.

Ventriculoatrial shunt: A shunt-valve system that moves (diverts) fluid from the ventricles of the brain to the right atrium of the heart.

Ventriculoperitoneal shunt: A shunt-valve system that moves (diverts) fluid from the ventricles of the brain to the abdominal cavity.

Abbreviations

CSF: Cerebrospinal Fluid
EDS External Drainage System
ELDS External Lumbar Drainage System
EVDS External Ventricular Drainage System
HPH: High Pressure Hydrocephalus
NPH: Normal Pressure Hydrocephalus
Pcsf: Intraventricular CSF pressure
Pei: Effective differential intraventricular CSF pressure, Pei=Pcsf−Pp
Pp: Intraparenchymal venous pressure
Psa: Subarachnoid space pressure
Pv: Extraparenchymal venous pressure (measured at Superior Sagittal Sinus (SSS))
Pvalve: Valve operating pressure
SSS: Superior Sagittal Sinus HPH and NPH develop through the interaction between different fluid pressures within the central nervous system.

As shown in FIG. 1, the superficial cerebral veins 105, which emerge from the brain surface and drain blood from the brain parenchymal sponge, travel through the subarachnoid space 115, submerged in Cerebrospinal Fluid (CSF), to join the dural venous sinuses and drain into the Superior Sagittal Sinus (SSS) 130. The normal pressure in the SSS 130 in a horizontal position is approximately 70 mm $H_2O$ (Pv=Extraparenchymal venous pressure, measured in the SSS).

The CSF also drains into the SSS 130, but through a different pathway, namely the arachnoid villi 135 in the SSS walls. The CSF pressure is a result of the resistance through these arachnoid villi 135 plus the pressure of the SSS 130. Therefore, the normal pressure of the CSF in the subarachnoid space 115 (Psa=Subarachnoid CSF pressure) is typically 120 mm $H_2O$ when the patient is in a horizontal position. Subarachnoid CSF pressure induces parallel variations in the intraparenchymal venous system pressure. Likewise, a venous pressure variation at the level of the SSS 130 or thereafter is transmitted to both intraparenchymal venous and CSF systems equally, because both drain into the SSS 130. These two mechanisms assure a constant hydrostatic loading of the brain tissue or sponge-like parenchyma 125.

The brain tissue or parenchyma 125 is subjected to two opposing pressures. One is produced by the CSF system (Pcsf), which tends to enlarge the ventricles 110 (and decrease the volume of the parenchyma 125; i.e., decrease the volume of the sponge). The other pressure is produced by the intraparenchymal venous system 120 (Pp), which tends to oppose ventricular volume enlargement and reduces the ventricular volume (and increases the volume of the parenchyma 125). As long as these two pressures remain equal regardless of their absolute values, the differential pressure between them is zero and the tissue is not submitted to the slightest degree of stress or distortion; the ventricular volumes, as well as the parenchymal volume, remain unchanged and in a steady-state condition.

The gradient that controls the degree to which liquids may be squeezed out of or into the parenchymal sponge and, in consequence, change and control ventricular volume and produce a specific form of hydrocephalus, is the differential existing between the intraventricular CSF pressure (Pcsf) and the intraparenchymal venous pressure (Pp). This gradient is designated the effective differential intraventricular CSF pressure (Pei=Pcsf−Pp). When Pcsf>Pp, then Pei>0 and the fluid is squeezed out of the parenchyma 125 (i.e., the sponge is "squeezed") and the ventricular volume increases. Conversely, when Pcsf<Pp, then Pei<0 and the fluid is allowed to fill the parenchyma 125 and enlarge the parenchymal volume and ventricular volume decreases. When ventricular volume enlargement is not opposed by an equal Pp and the ventricles dilate, symptoms of NPH (even at normal Pcsf) are produced.

In a normal brain 100, the pressure of the Cerebrospinal Fluid within the Ventricles (Pcsf) 110 is typically equal to the pressure of the Intraparaenchymal Venous Pathways (Pp) 120. Thus, when Pcsf=Pp, no gradient exists between these two pressure compartments that would cause the ventricles to enlarge, ventricular volume remains normal and hydrocephalus does not develop. Hydrocephalus or the enlargement of the volume of the ventricular cavities in the brain 100 is produced by a pressure imbalance (i.e. gradient between Pcsf and Pp) in the brain 100 and may occur when either Pcsf 110 becomes greater than Pp 120 (as is the case of High Pressure Hydrocephalus), or when Pp 120 becomes less than Pcsf 110 (as is the case in Normal Pressure Hydrocephalus). The goal in the management of hydrocephalus is to manipulate CSF pressure (Pcsf) such that it is lower than or equal to Parenchymal pressure (Pp).

Early shunts (consisting of an inflow catheter, a valve, and a drainage catheter) for the treatment of hydrocephalus, incorporated fixed pressure valves to regulate flow through the shunt. In many cases, after the implantation of a fixed pressure valve, a physician would need to perform several surgeries to replace the initial valve, due to under-drainage or over-drainage, with one of a different operating pressure range (e.g., lower pressure range for underdrainage or higher-pressure range for overdrainage) until the optimal operating pressure range (equilibrium conditions) was determined. Externally (non-invasively) adjustable, "programmable" valves have been developed, in which the operating pressure of the valve can be adjusted noninvasively (through the skin) rather than using surgery to replace the valve. However, it is generally necessary to frequently adjust the pressure setting of such programmable valves to optimize shunt performance. This is achieved through one or more visits to the clinician. Once programmed, adjustable valves act like fixed pressure valves (i.e., do not adjust to the patient's changing requirements) until reprogrammed based upon the clinical judgment of the clinician. This limits when such a valve may be adjusted to the needs of the patient to visits to the clinician and does not allow for accommodation of the patients' daily requirements with valve adjustments based upon the patient's changing clinical needs throughout the day.

Aspects and embodiments are directed to a self-adjusting valve that may continuously determine the required valve resistance and adjust accordingly without the need for clinician intervention.

Conventional shunt valves in use today, either fixed pressure or non-invasively adjustable valves, work with two parameters: an inlet pressure (CSF), and an outlet drainage pressure (either right atrium of the heart (essentially zero pressure) or peritoneal cavity pressure). These devices control the CSF pressure allowing CSF to flow through the valve until the pressure of the CSF drops below that of the operating pressure setting of the valve system. Even though the physician can use some parameters such as ventricular volume and CSF pressure as a guide for setting the valve operating pressure, there is some trial-and-error involved in valve selection (fixed-pressure valves) or adjustment (variable-pressure valves). In contrast, aspects and embodiments are directed to a self-adjusting valve using a third parameter that provides the feedback to automatically control the adjustment of the pressure setting of the valve and therefore provide a closed-loop system to spontaneously and continuously adjust the valve whenever and wherever necessary without intervention of a clinician.

According to an early understanding of the brain, in a healthy patient, the subdural pressure had a value of zero because the brain tissue would absorb the CSF pressure from the ventricles. As a patient develops hydrocephalus and the ventricles increase in volume and/or the CSF pressure increased in value, more of the ventricular pressure would be transmitted through the brain tissue or parenchyma, to the surface of the brain and the subdural pressure would have a positive value. Conventional self-adjusting valves were based on the concept that the subdural pressure in a normal person was equivalent to zero. Only when a person developed hydrocephalus, the subdural pressure would have a value above zero, and this would be used to lower the pressure setting of the valve to drain CSF.

According to certain aspects, from a newer understanding of the hydraulics of the cranial cavity, as well as from experimental evidence, one can conclude that the subdural pressure in a healthy subject will not have a value of zero. Instead, the subdural sensor will measure the higher of the two pressures, Pcsf and Pp. Accordingly, aspects and embodiments of a self-adjusting valve are based, at least in part, on the recognition that a parenchymal pressure sensor measures the higher of the intraparenchymal venous pressure (Pp) and the intraventricular CSF pressure (Pcsf). The Pcsf can be measured directly using a sensor placed in the CSF. Therefore, by comparing the pressure reading from a subdural sensor probe and the pressure reading from a CSF pressure sensor, an observer or a system can extrapolate the Pp.

More specifically, in the starting state, a patient with High Pressure Hydrocephalus (HPH) has a high Pcsf and a normal Pp, (i.e., Pcsf>Pp). At the starting point, the parenchymal sensor measures the Pcsf, because Pcsf is higher than Pp. The CSF pressure sensor, which also measures the Pcsf, may give the same reading as the parenchymal sensor. The valve may then be set to allow the patient's Pcsf to decrease slowly. As the Pcsf begins to decrease, the parenchymal sensor and the CSF sensor will continue to give the same reading. However, once the patient's Pcsf drops below the Pp, the parenchymal sensor will begin to measure the Pp instead. At this point, the system or observer can know that Pcsf<Pp because the parenchymal sensor and the CSF sensor are measuring different pressure readings. The valve can retain this setting for long enough to allow the ventricles to normalize (i.e., drain to a physiologically normal volume). The valve can then be adjusted to equalize Pcsf and Pp to maintain steady-state equilibrium. As discussed further below, aspects and embodiments disclosed herein provide systems and methods of equalizing the Pcsf and Pp, thereby correcting the pressure imbalance that causes ventricular volume enlargement and, thus treating a patient with HPH or NPH.

Certain aspects are also based, at least in part, on the recognition that Normal Pressure Hydrocephalus (NPH) is characterized by pressure imbalance in the brain, with a normal Pcsf and a lower than normal Pp, (i.e., Pcsf>Pp). Aspects and embodiments disclosed herein provide systems and methods for equalizing the Pcsf and Pp, thereby correcting the pressure imbalance that causes ventricular volume enlargement under normal Pcsf pressures and thus treating the patient with NPH. These pressure-relationship concepts for non-hydrocephalic conditions, HPH and NPH are summarized in the following table:

| Condition | Pressures Measured | Observations | Objective | Treatment Method |
|---|---|---|---|---|
| Normal~ Steady State (No hydrocephalus) | Pcsf = Pp | Ventricular pressure is normal; parenchymal pressure is normal. System is in equilibrium. | No intervention necessary | None required |
| HPH | Pcsf > Pp | Ventricular pressure is elevated; parenchymal pressure is normal | Reduce ventricular volume by reducing pressure gradient | Reduce valve pressure setting for Pcsf < Pp, until ventricles are normal volume. Then |

-continued

| Condition | Pressures Measured | Observations | Objective | Treatment Method |
|---|---|---|---|---|
| | | | between Pcsf and Pp. | increase Pcsf until it reaches its normal value, and maintain Pcsf equivalent to Pp. |
| NPH | Pcsf > Pp | Ventricular pressure is normal; parenchymal pressure is reduced below Pcsf | Reduce ventricular volume by reducing pressure gradient between Pcsf and Pp. | Reduce valve pressure setting for Pcsf < Pp, until ventricles are normal volume. Then increase Pcsf to maintain equivalent to Pp. |

Advantageously, some patients recover remarkably, even though the ventricles do not decrease much in size. In some cases, it may be sufficient to simply reduce the pressure gradient that produced enlarged ventricles, for the patients to recover. In other words, it may not be completely necessary for the ventricles to reduce to normal volume for the patient to recover. Accordingly, certain aspects are directed primarily to reducing the pressure gradient between Pcsf and Pp.

For patients with High Pressure Hydrocephalus (HPH), Pcsf 110 is higher than normal (due to a partial obstruction in the CSF circulation) and Pp 120 is normal, therefore, Pcsf>Pp. For patients with Normal Pressure Hydrocephalus (NPH), Pcsf 110 is normal (because there is no obstruction in the CSF circulation), but Pp 120 is below normal; therefore: Pcsf>Pp.

Figure 2A:
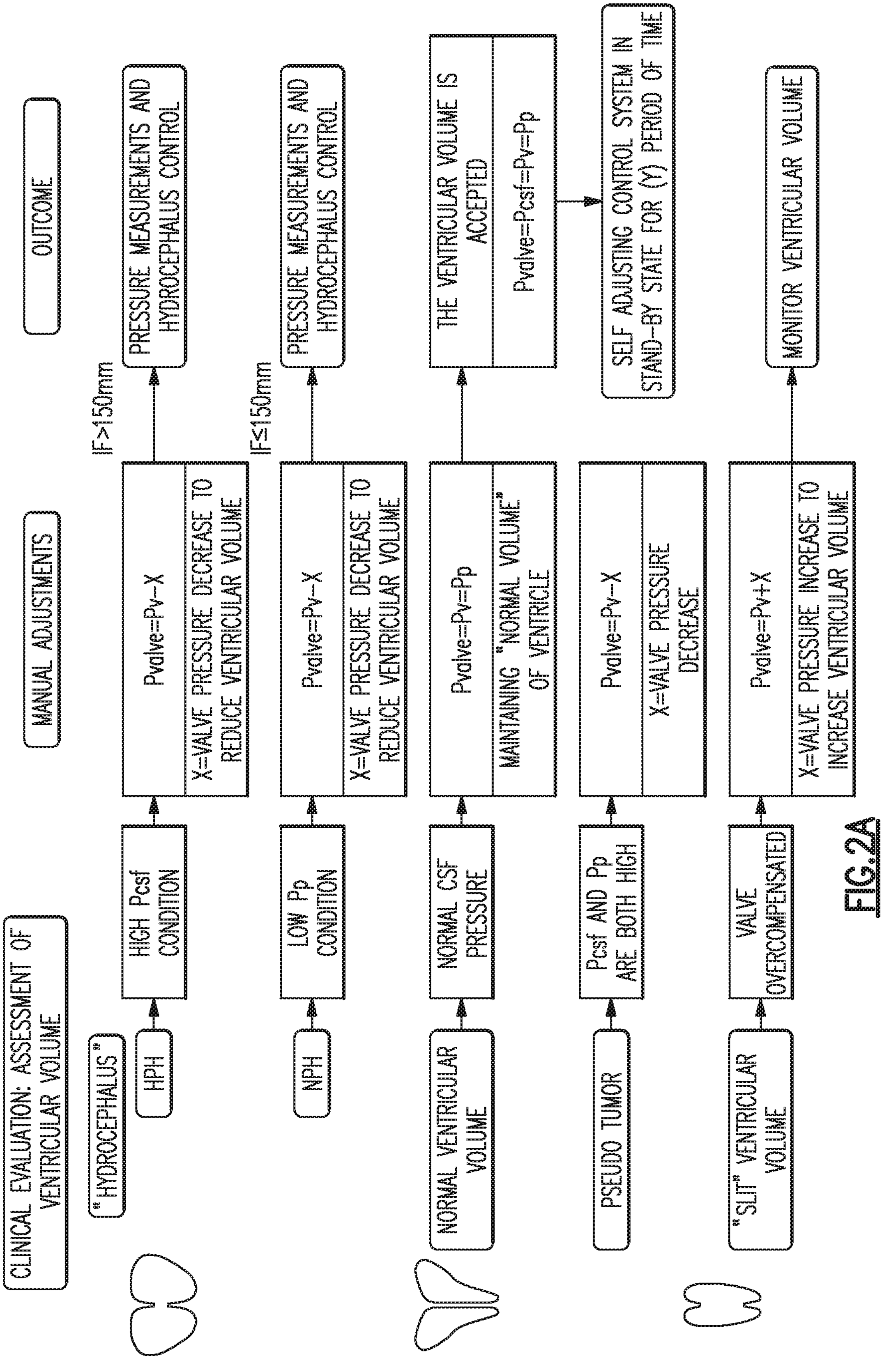
FIG. 2A is a graphical representation of an algorithm for the clinical evaluation by a physician for a self-adjustable valve for various clinical conditions.

FIG. 2A provides a graphical representation of the process by which the physician may visually, through clinical means (e.g., imaging), assess the patient's condition for the ventricular volume to determine whether there is an existing hydrocephalus condition. The visual imaging assessment may be done, for example, with an MRI or CT-scan. If the clinical evaluation is indicative of enlarged ventricles associated with hydrocephalus, then the valve pressure setting may be decreased to reduce ventricular volume. A hydrocephalus condition may be assessed as either High Pressure Hydrocephalus (HPH) or Normal Pressure Hydrocephalus (NPH). For both cases, the manual adjustments are the same. If the ventricular volume is determined to be normal size, the hydrocephalus control system may measure the Pcsf and Pp pressures and may be programmed to a "standby", steady-state mode of monitoring the CSF pressure and the intraparenchymal venous pressure as the hydrocephalus will be in an arrested state. However, a normal ventricular volume with a high Pcsf and high Pp may be indicative of a pseudo tumor condition. In this case, the valve pressure can be reduced to allow Pcsf and Pp to decrease to normal values. If the assessment indicates that the ventricles are in a "slit" condition (known as slit- or smaller than normal ventricles), the valve pressure setting may be increased to allow the ventricular volume to enlarge ("normalize"). The ventricular volume may be visually monitored to assess whether the ventricles return to a normal size.

Figure 2B:
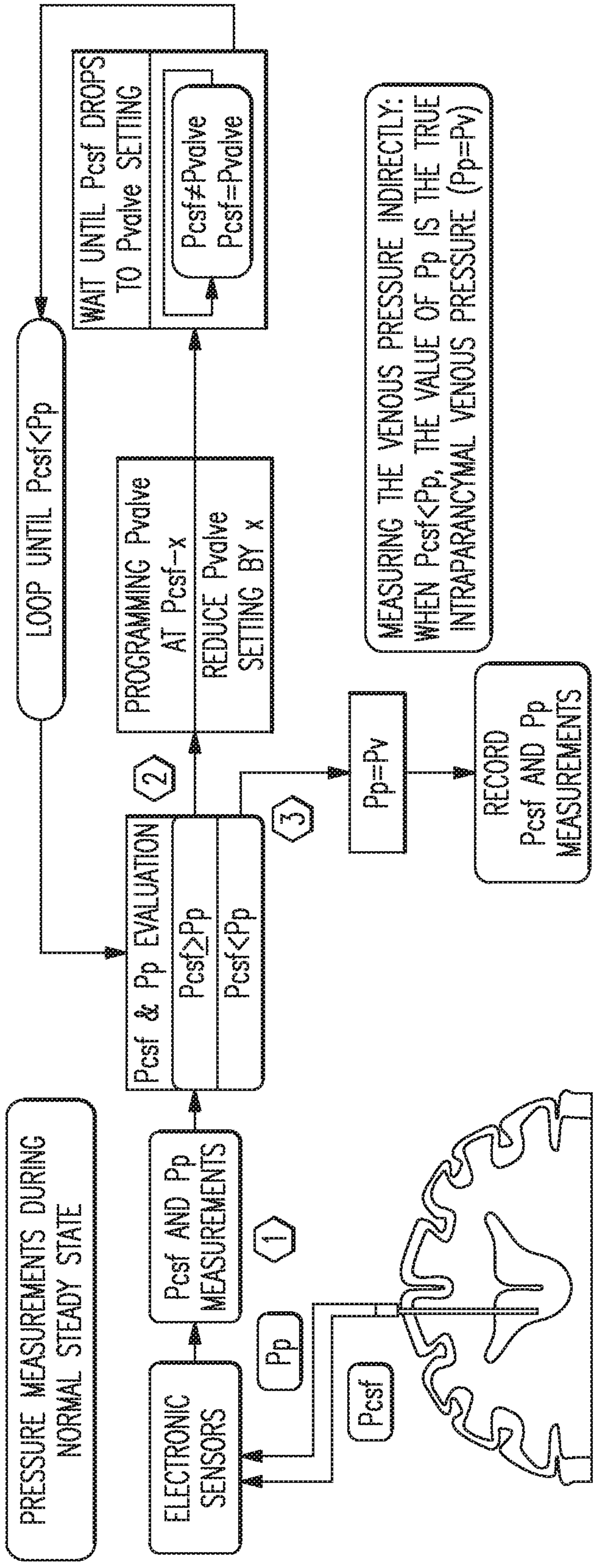
FIG. 2B a graphical representation of an algorithm for the measurement and treatment with a self-adjustable valve of a patient diagnosed with hydrocephalus.

FIG. 2B provides a graphical representation of an algorithm for a self-adjustable valve. Step 1 shows that there may be electronic sensors (i.e. pressure transducers) which may measure the intraventricular CSF pressure (Pcsf) and the intraparenchymal venous pressure (Pp). The Pcsf and Pp pressure measurements may be compared to determine whether they may be equal, or whether Pcsf may be greater than or equal to Pp, or whether Pcsf may be lower than Pp. If Pcsf is not lower than Pp (step 2), then the Pp measurement may not yet be the actual extraparenchymal venous pressure (Pv). The valve pressure setting may be reduced in a closed loop algorithm of changing the valve pressure setting, waiting for a set period, and measuring the two pressures, until Pcsf is lower than Pp. Once Pcsf is lower than Pp (step 3), it may then be assumed that the Pp may reflect the actual extraparenchymal venous pressure (Pv).

Figure 2C:
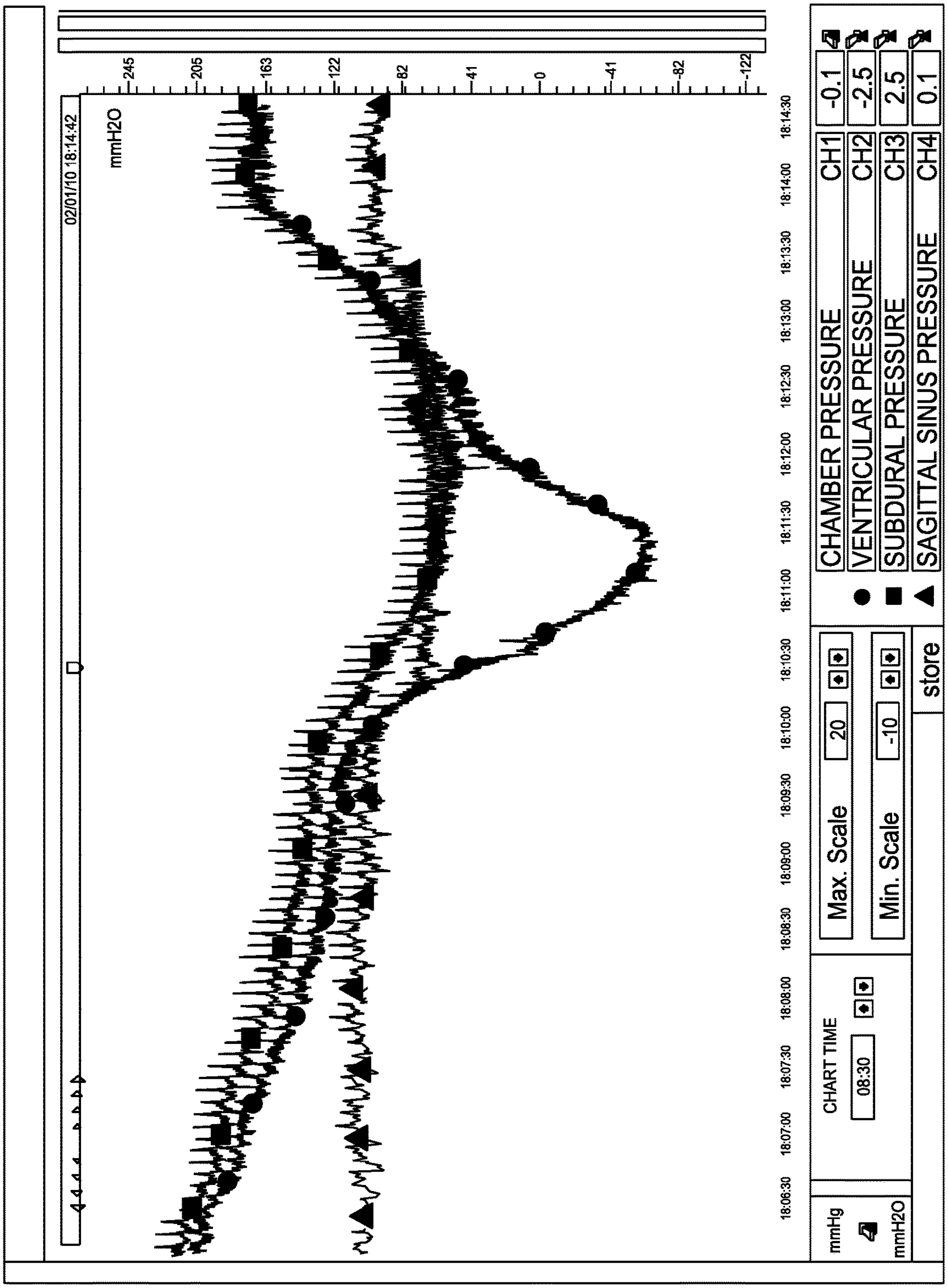
FIG. 2C is an illustration of an example of laboratory research data for pressure measurements and a graphical representation of the pressure measurements described herein.

FIG. 2C provides an example of evidence, based on research data that a sensor implanted in the subdural region of the cranial cavity measures the higher of intraparenchymal venous pressure (Pp) and the cerebrospinal fluid pressure (Pcsf). In a healthy subject, these two pressures are typically equal. In contrast, in HPH, NPH, or pseudo tumor (a condition with elevated intracranial pressure and no ventricular enlargement), a sensor in the subdural region may not necessarily measure the intraparenchymal venous pressure. A sensor, transducer or other device used to measure a particular variable pressure in the cranial cavity, tends, to some degree, measure all other variables in the environment and will therefore measure the highest pressure among the different fluids. In the three conditions mentioned above (i.e., HPH, NPH, or pseudo tumor), a sensor in the subdural area would only be a direct measurement of intraparenchymal venous pressure (Pp) if this were the higher pressure out of Pp and Pcsf.

| Condition | Ventricles | ICP |
|---|---|---|
| HPH | Ventricles are dilated because the Pcsf is higher than normal (above 200 mm $H_2O$) and above Pp (intraparenchymal venous pressure) | When intracranial pressure is measured, the value is that of the Pcsf. |
| NPH | Ventricles are dilated because Pp (intraparenchymal venous pressure is lower than normal (approximately 80 mm $H_2O$) and lower than Pcsf (which is at its normal value of approximately 120 | When intracranial pressure is measured, the value is that of the Pcsf |

-continued

| Condition | Ventricles | ICP |
|---|---|---|
| | mm $H_2O$). | |
| Pseudotumor cerebri | Ventricles are not dilated, even though both Pcsf and Pp can be quite elevated, sometimes above 500 mm $H_2O$. The ventricles do not dilate because these two pressures (Pcsf and Pp) are equal and oppose each other and the differential pressure is zero. | When intracranial pressure is measured, the value is that of the Pcsf and Pp, which are equal. |

From this, one can conclude that the pressure that is measured is always the higher of the two pressures. Accordingly, certain aspects are directed to methods of measuring the Pp and Pcsf independently. Based on the hypothesis that under normal conditions the CSF pressure controls the intraparenchymal venous pressure, the following experiment was designed, and the results are illustrated in the graph in FIG. 2C.

Simultaneous measurements were performed in a normal dog for the following:

Ventricular CSF pressure (plot indicated by circular label)

Subdural pressure (plot indicated by square label)

Superior Sagittal Sinus pressure (plot indicated by triangle label)

As the pressures were being recorded, ventricular CSF pressure (plot with round label) was slowly reduced by lowering a bag filled with saline solution that was connected to the ventricles. It was observed that as ventricular CSF pressure (Pcsf) decreased; this produced an equal reduction of pressure in the subdural sensor (plot with square label). As is seen on the left portion of the graph, both pressures continued to decrease until they reached the value of the superior sagittal sinus pressure (plot with triangle label), at which point the Pcsf continues to drop but the subdural pressure does not decrease further (i.e., below Pv in the SSS). At this moment, the subdural sensor is now measuring intraparenchymal venous pressure (Pp), which cannot go below the value of the superior sagittal sinus pressure (abbreviated as Pv, and Pv=Pp in the central portion of this graph). In the central portion of the graph, the Pcsf is lower than the Pp, and the subdural sensor measures the Pp. Later, as the ventricular CSF pressure is increased by raising the bag filled with saline, intraparenchymal venous pressure, as measured by the subdural sensor, only begins to increase once the CSF pressure is above the value of the superior sagittal sinus pressure (Pv) (as shown on the right portion of the graph).

Figure 3A:
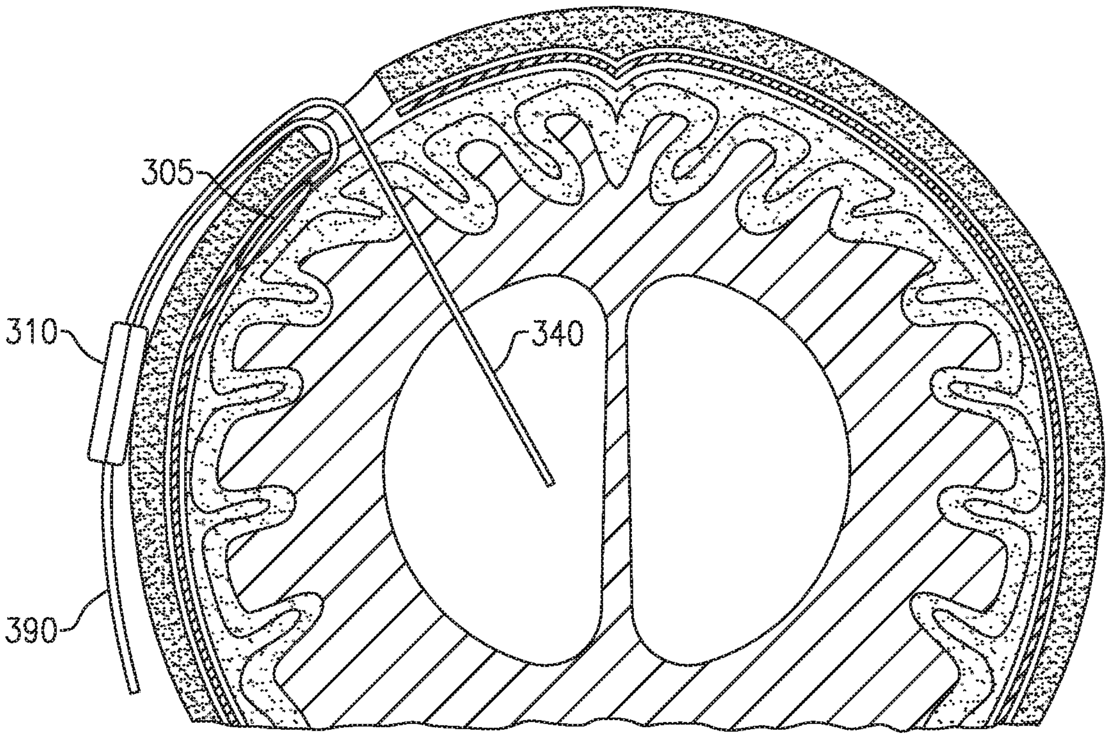
FIG. 3A is a diagram illustrating device components of an example of the self-adjusting hydrocephalus valve system based on a mechanical design approach.

As illustrated in FIGS. 2A and 2B and described further below, the fundamental principle of the true measurement of the intraparenchymal venous pressure may be implemented as either a mechanical regulated system, or as a sensor-based electronic regulated control system. FIG. 3A illustrates an example of a mechanically designed self-adjusting valve. The hydrocephalus adjustable valve 310 may include a ventricular catheter 340, which may be implanted into the ventricle of the brain which may provide the Pcsf measurement. The pressure that may also be used as the feedback to a mechanically controlled hydrocephalus valve system, may be the contact pressure at the surface of the brain, as exemplified as a subdural pressure bag 305. The self-adjusting valve 310 may reduce the pressure mechanically with the intent to maintain equivalency between the Pcsf and subdural pressures. The adjustable valve 310 may also be connected to a distal outflow drainage catheter 390 and located external to the skull.

Figure 3B:
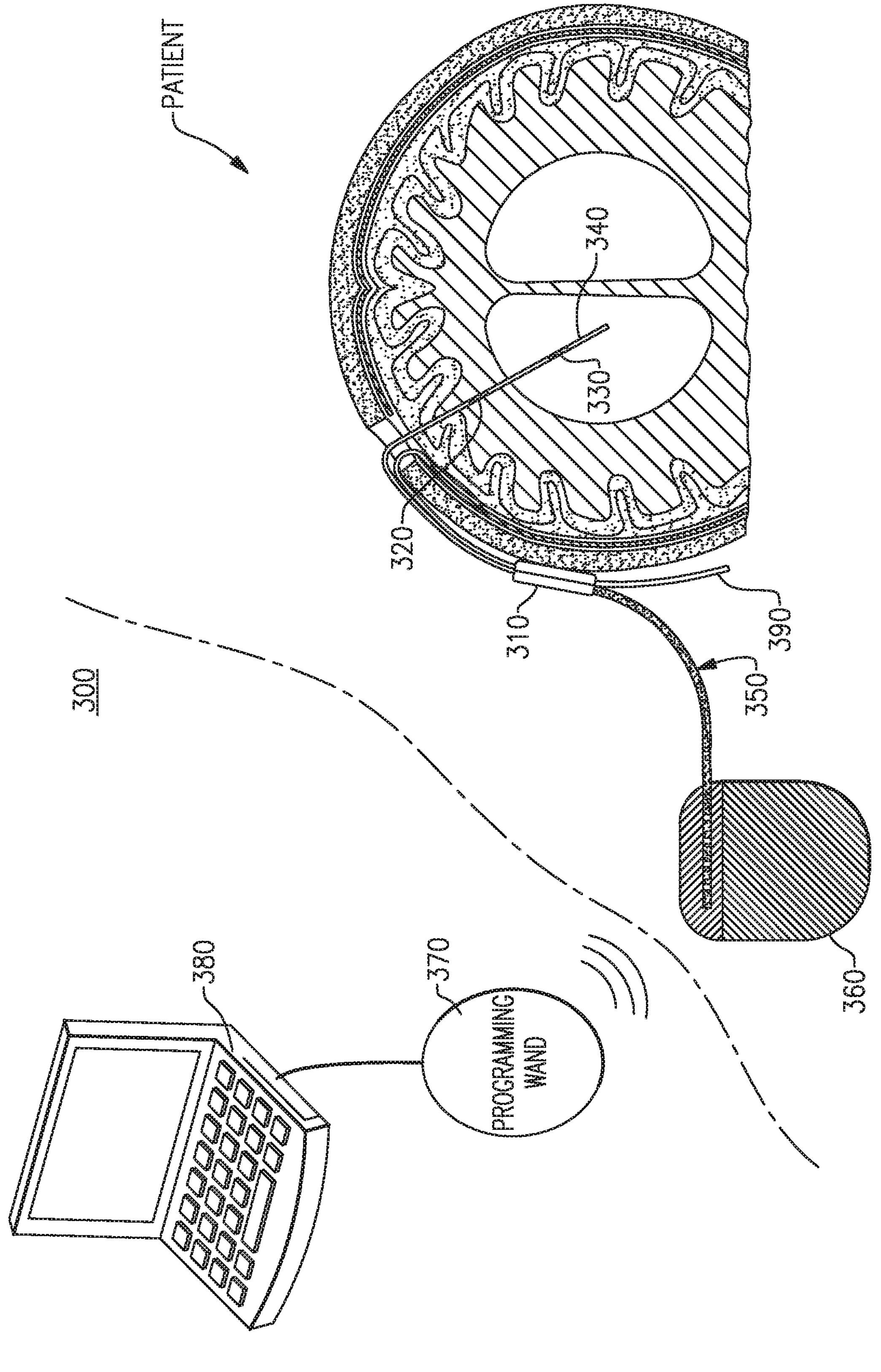
FIG. 3B is a diagram illustrating device components of an example of the self-adjusting hydrocephalus valve system.

FIG. 3B illustrates device components of an example of a self-adjusting hydrocephalus valve system 300. As discussed above, the hydrocephalus adjustable valve 310 may include a ventricular catheter 340 which may be implanted into the ventricle of the brain. In certain examples the ventricular catheter 340 may be connected to or be part of an external ventricular drainage system used to control the drainage of CSF from the brain or spinal subarachnoid space with displays of sensor outputs and data processing to provide physiologically-relevant data. An electronic CSF pressure sensor 330 may be mounted on the outer surface of the ventricular catheter 340 and may be capable of measuring the CSF Pressure (Pcsf) in this fluid space. A second electronic pressure sensor 320 may also be externally mounted on the ventricular catheter 340 in a location in contact with the brain parenchyma and may be capable of indirectly measuring the Intraparenchymal Venous Pressure (Pp). The adjustable valve 310 may be connected to the distal outflow drainage catheter 390 and located external to the skull. A second catheter or valve communications cable 350 may include the electrical connections or wires of the CSF pressure (Pcsf) sensor 330, the intraparenchymal venous pressure (Pp) sensor 320, and the electronic control signal to change the pressure settings of the adjustable valve 310. The valve communications cable 350 may also be connected to a valve controller 360, which may include an implanted electronic valve control device and power source, and which may provide the information upon which valve adjustments are based.

According to certain embodiments, the valve controller 360 may include a power source, a microcontroller, and a wireless communications circuit (not shown in FIG. 3B) and is described further below with reference to the block diagram of FIG. 8. The power source may be a primary battery, a rechargeable battery, or device that may receive a continuous wireless power transfer from an external power source (or may be a combination of two or more of these elements). The microcontroller within the valve controller 360 may analyze the pressure measurements taken by the two pressure sensors and may determine actions to be taken for changing the settings of the adjustable valve 310 based on each measurement. Examples of these algorithms are discussed in further detail with reference to the flow chart presented in FIG. 6. Wireless communications may provide the ability for the clinician to retrieve stored recorded pressure measurements, instruct the implanted valve controller 360 to perform specified operations, retrieve the current programmed operational settings of the valve controller 360, and to reprogram (adjust) the operational settings of the adjustable valve 310 and the implanted valve controller 360. The electronics of the valve controller 360 may be encased within a hermetically-sealed enclosure (constructed of titanium or similar material) as is typical for active implantable medical devices. An external programmer 380 may provide a graphical user interface for reviewing the information retrieved from the implanted valve controller 360. In addition, the external programmer 380 may provide the transcutaneous wireless communications which may retrieve the data from the valve controller 360 through a programming wand 370 which may receive the wirelessly-transmitted data for review and archiving by the physician, as well as transferring the programmed data to allow the physician to adjust the operational settings in the valve controller 360 to control the adjustable valve 310.

Figure 3C:
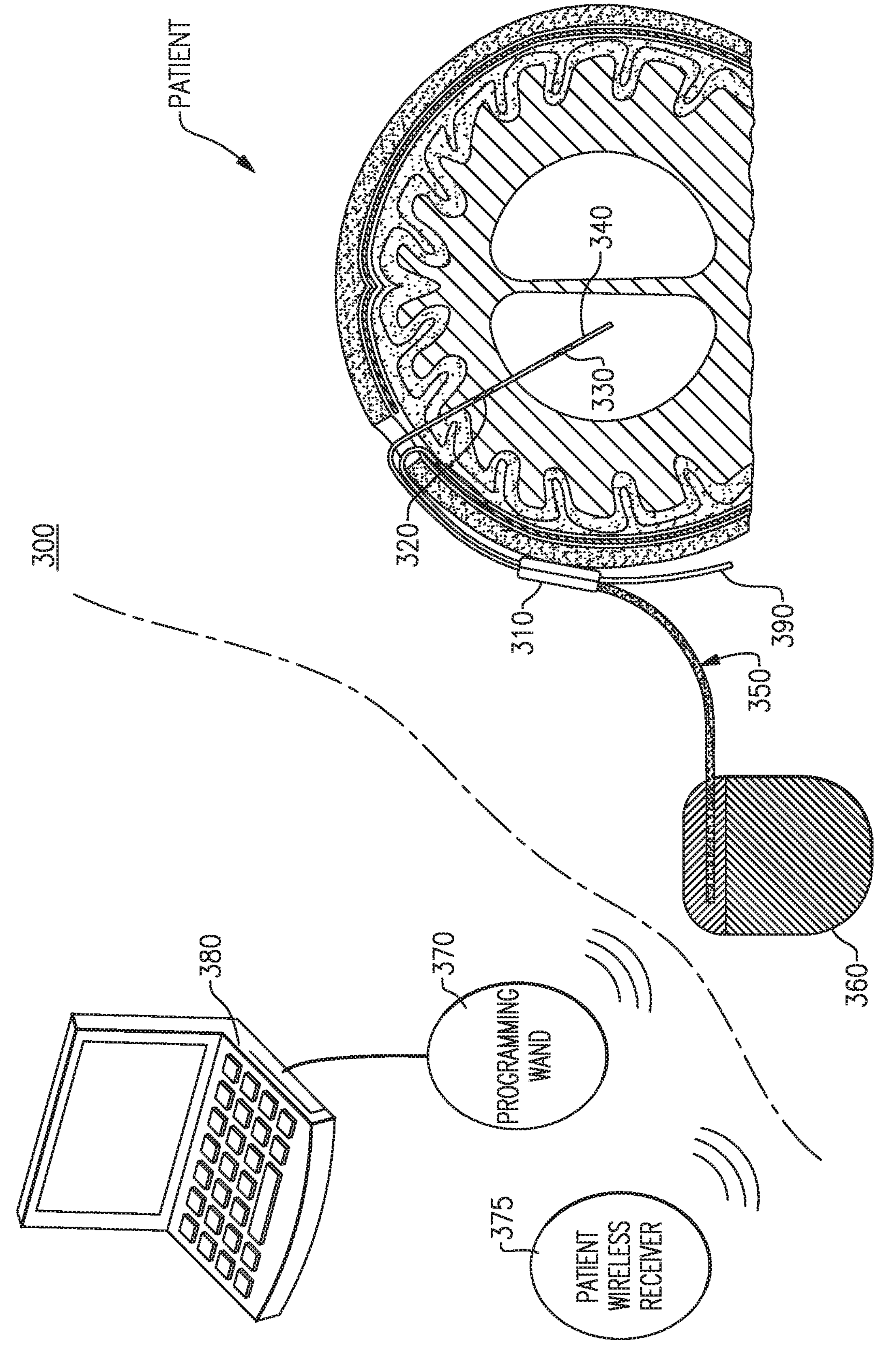
FIG. 3C is a diagram illustrating another example of device components of the self-adjusting hydrocephalus valve system, which also includes a portable wireless receiving device.

FIG. 3C provides a variation of the system components. In the example shown in FIG. 3C, all the components are the same as in FIG. 3B, except that there may be an additional external device or a patient wireless receiver 375, which may be carried by the patient or caregiver. The patient wireless receiver 375 may receive wireless communications from the implanted valve controller 360. The wireless communications may be initiated by the valve controller 360 and sent to the patient wireless receiver 375 as the result of an alarm condition identified by the valve controller 360, for example. The alarm condition may be the result of a pressure measurements from either the CSF pressure (Pcsf) sensor 330, the intraparenchymal pressure (Pp) sensor 320, and/or the differential intraventricular CSF pressure (Pei=Pcsf−Pp). The alarm may also be generated as the result of a condition identified during a self-diagnostic check of the implanted system by the valve controller 360.

Figure 4:
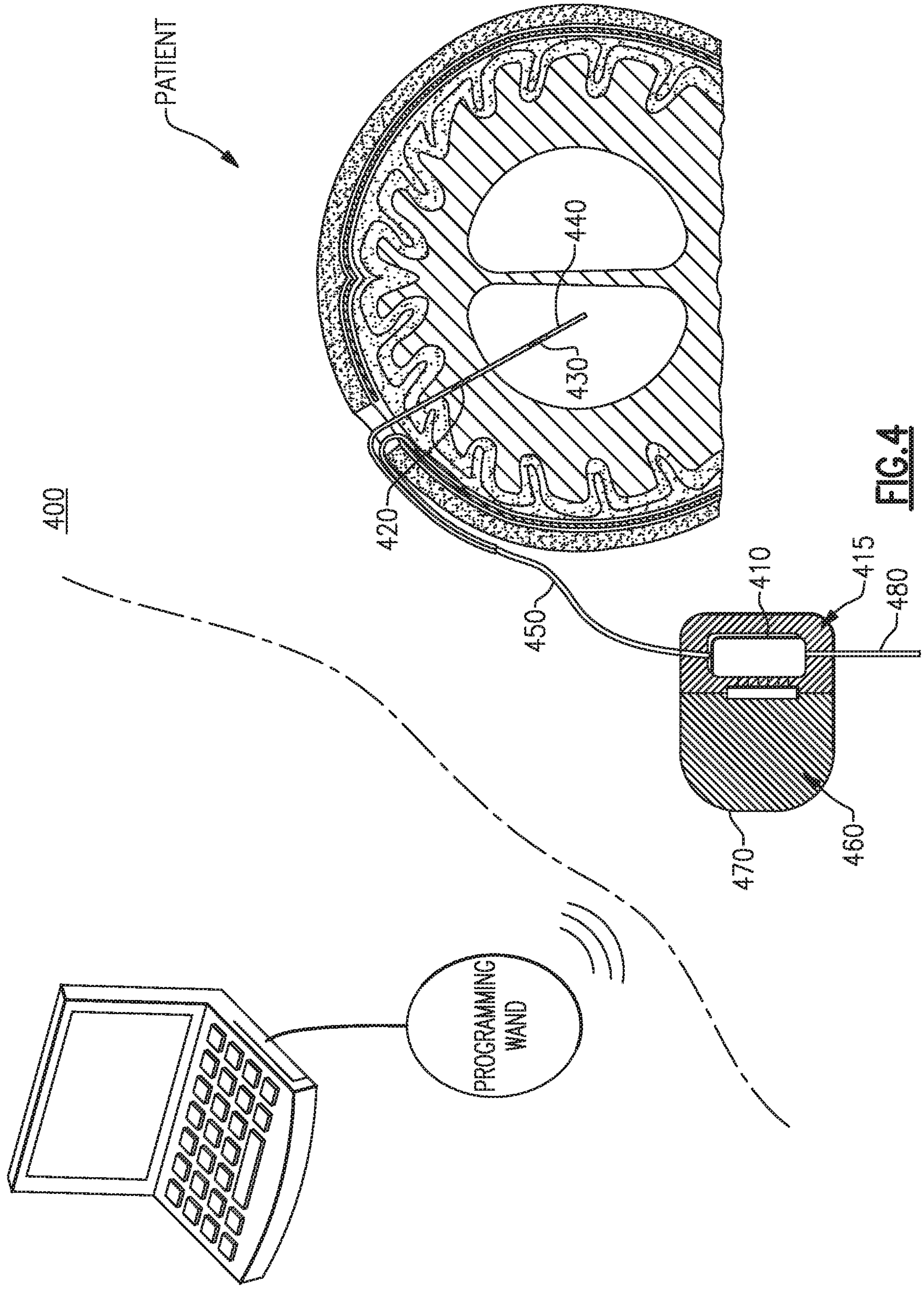
FIG. 4 is a diagram illustrating a configuration of device components providing another example of the self-adjusting hydrocephalus valve system with an integrated controller and adjustable valve.

According to another embodiment, an example of which is illustrated in FIG. 4, a self-adjusting hydrocephalus valve system 400 includes an adjustable valve 410 and a valve controller 460 that can be integrated and physically assembled into one implanted self-adjusting valve/controller device 470. As with the device shown in FIG. 3B, the electronics of the valve controller 460 may be encased within a hermetically-sealed titanium enclosure. The adjustable valve 410 may be encased in a polymer header 415. A drainage catheter 480 may exit the adjustable valve 410 through the polymer header 415. The self-adjusting valve/controller device 470 may also allow for a simpler ventricular catheter 440 and wire connections between the intraventricular CSF pressure sensor 430 and intraparenchymal venous pressure sensor 420 and the adjustable valve 410 as a single ventricular or lumbar catheter and pressure sensor wire 450. The electrical connections between the valve controller 460 and the adjustable valve 410 may be contained within the self-adjusting valve/controller device 470.

Figure 5:
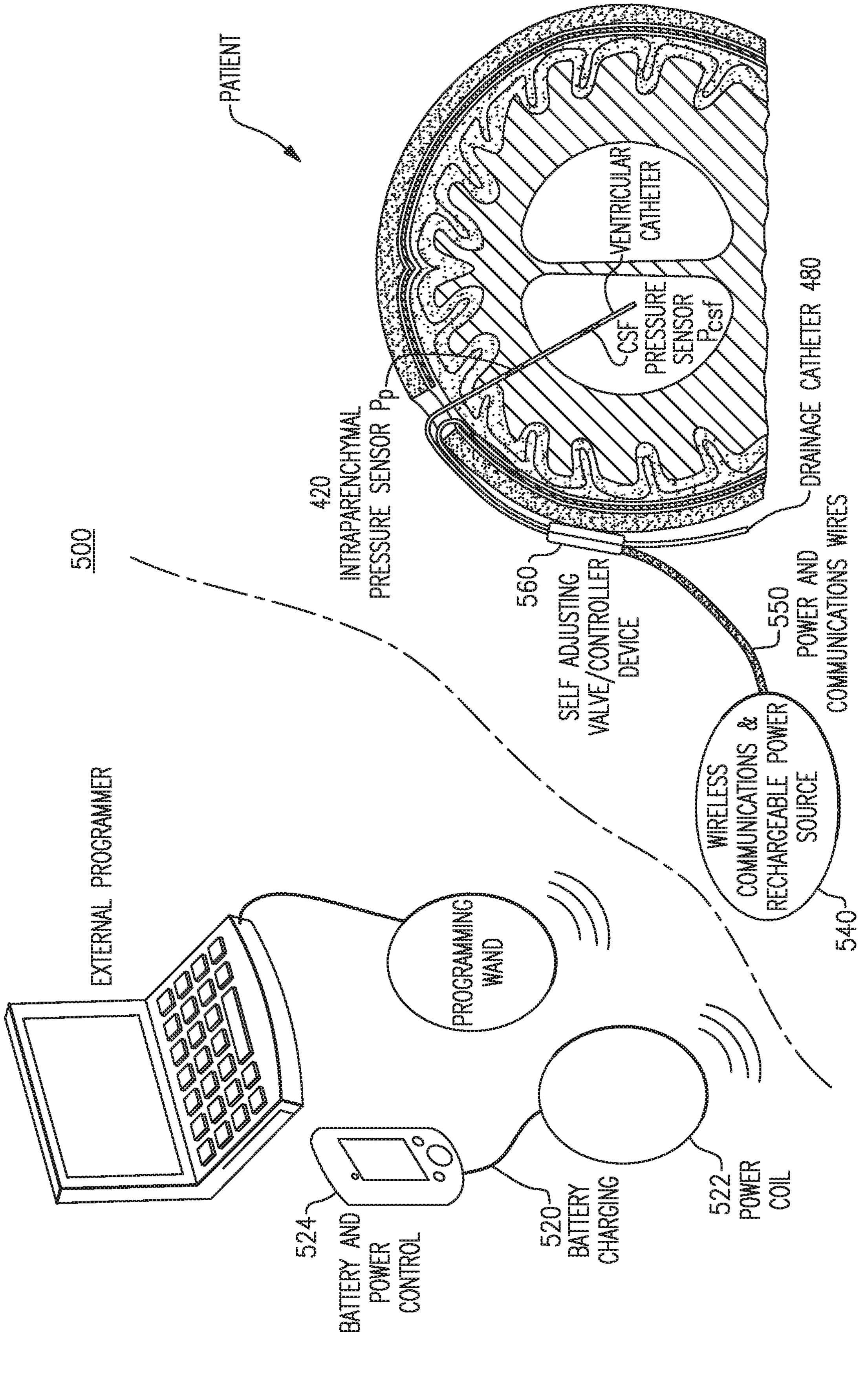
FIG. 5 is a diagram illustrating a configuration of device components providing another example of the self-adjusting hydrocephalus valve system with an integrated controller and adjustable valve with a rechargeable power source.

Another embodiment of a self-adjusting hydrocephalus valve system 500 is shown in FIG. 5. In this example, the self-adjusting valve/controller device 560 may still be integrated but may configure the power source and wireless communication as a separate module 540. This configuration may provide an advantage of a smaller self-adjusting valve/controller device 560 resulting in shorter drainage catheters and sensor wires to the self-adjusting valve/controller Device 560. The power source in this embodiment may also include a rechargeable battery, which allows for a longer-term implant duration and/or smaller battery option. An implanted wireless communications and rechargeable power source 540 may be located remote from the self-adjusting valve/controller device 560. A wireless power transfer between an external battery charger 520 and the wireless communications and rechargeable power source 540 may transfer the power from a power coil 522 to a coil within the wireless communications and rechargeable power source 540. Power for charging the wireless communications and rechargeable power source 540, may be provided by a portable (e.g., patient wearable) battery and power control 524 devices, or it can be provided from an AC adapter (not shown).

Figure 6:
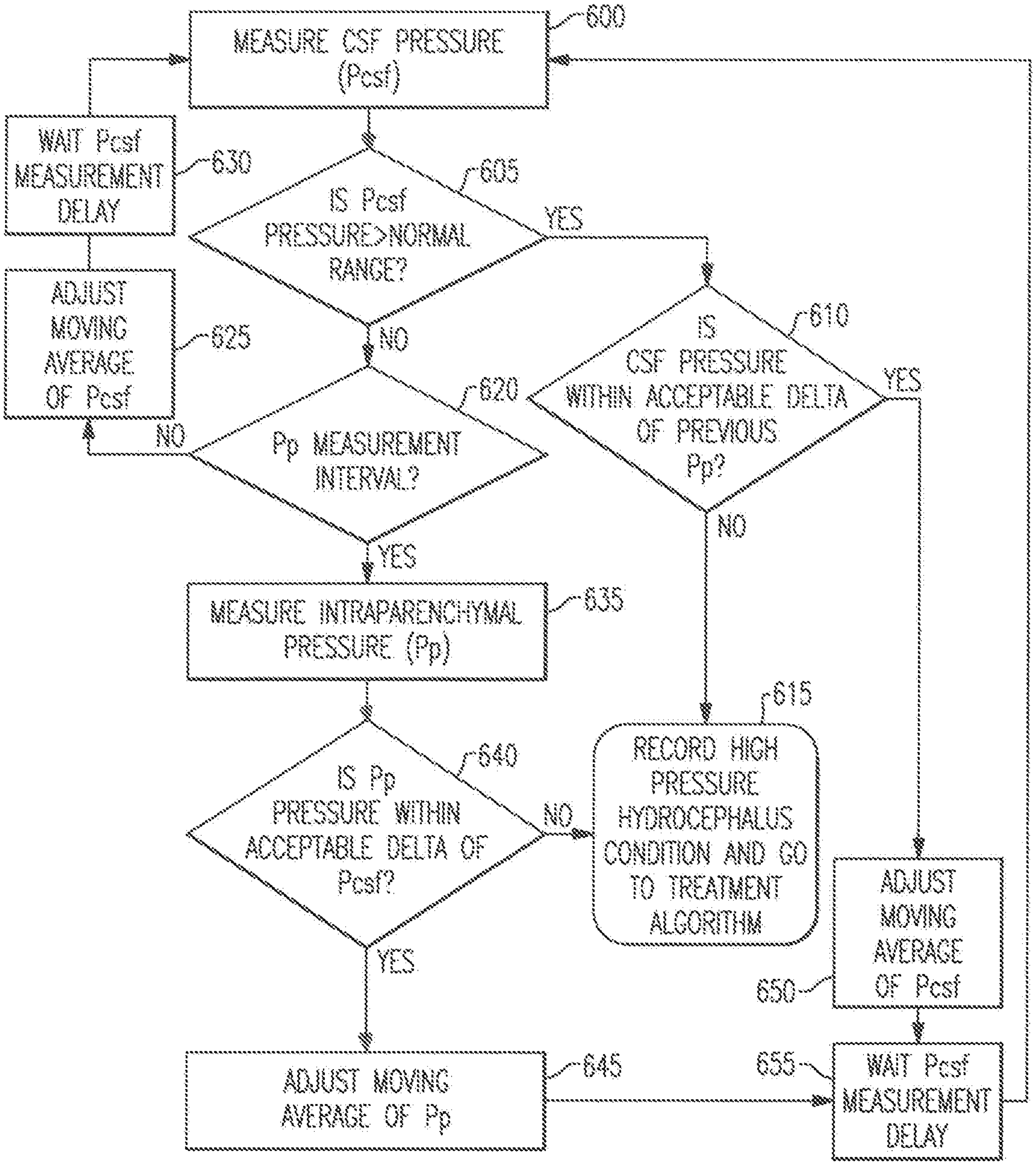
FIG. 6 is a flow chart of an example of the measurement and monitoring of the CSF pressure (Pcsf) and Intraparenchymal Venous Pressure (Pp) in the determination of the presence of a hydrocephalic condition.

An example of a process for the determination of the recurrence of hydrocephalus during steady state monitoring over predetermined intervals is shown as a flow chart in FIG. 6. In this example, the measurement and continuous monitoring of the CSF pressure (Pcsf) 110 and intraparenchymal venous pressure (Pp) 120 is performed with the CSF pressure (Pcsf) sensor 330 and intraparenchymal pressure (Pp) sensor 320 shown in FIG. 3B. This monitoring process may also allow the valve controller 360 to record and identify the variations of Pcsf over the course of a day (or other period) to account for the patient's circadian rhythm as well as the patient's changing posture as parametric factors to consider when determining whether there may be a potential hydrocephalic condition developing.

Referring to FIG. 6, in step 600, the process encoded within the valve controller 360 may start by taking a pressure measurement from the CSF pressure (Pcsf) sensor 330. The Pcsf measured value may be compared to a predetermined Pcsf value, and the process may include a step 305 of identifying whether the measured Pcsf may be within a predetermined normal range for the patient as stored within the memory of the valve controller 360. If the Pcsf is within the normal range of Pcsf, the step 610 may include determining whether the Pcsf is within an acceptable difference (or delta) pressure from the previously measured Pp. If the pressure delta is within a normal range of Pp, then the Pcsf may be factored into a moving average calculation in step 650 to account for variations in Pcsf throughout the day. The process then may wait for a programmed Pcsf measurement delay period 655 (e.g., 1 hour), before taking the next Pcsf measurement 600. If in step 605 it is determined that the Pcsf value is not within the patient's normal Pcsf range, the step 620 may include determining whether there is a sufficient time interval (e.g., 3 hours) since the last Pp measurement. The process may also include taking multiple sequential measurements (not shown in flow chart) of Pcsf to verify that the increased differential pressure for Pp is not caused by an anomalous measurement (e.g., noise). With the Pp measurement interval longer than the Pcsf measurement interval, the verification of the Pcsf over this longer interval in step 620 may provide the measurement process the ability to confirm that the Pcsf may be out of range. Similar to Pcsf measurements, confirmation through repetitive measurements may filter out any measurement noise artifacts before proceeding to the measurement of the Pp. Taking repetitive measurements to confirm valid pressure values may also apply to other conditions throughout the process when it is suspected that a significant pressure deviation may have potentially occurred. If the Pp measurement interval has not been reached in step 620, then the Pcsf measurement value may be factored into a moving average calculation in step 625 and the process may then wait for a specified Pcsf measurement delay period 630 before taking the next Pcsf measurement in step 600. If in step 620 the Pp measurement interval has been reached, the Pp may be measured in step 635. Examples of a method of determining whether the measurement from the Pp sensor 330 may be representative of the actual intraparenchymal venous pressure are discussed further below with respect to FIG. 7. If the Pp is within acceptable delta limits of Pcsf as determined in step 640, a normal non-hydrocephalus condition may be identified, and the Pp measurement may be calculated into a Pp moving average 645. The process may then proceed to step 655 to wait for the next Pcsf measurement delay. If the Pp measurement is not within an acceptable delta of the Pcsf 640, then the valve controller 360 may record the Pp value and may identify the condition as hydrocephalus in step 615, and may alert the patient through wireless communications, and then proceed to a treatment process. The physician may also program the valve controller 360 to provide only an alert to the patient of a pressure measurement deviation with the instructions to contact their physician. The measured data may be remotely transmitted to the physician for review. The physician may either remotely reprogram the valve controller 360 or request the patient to go to a medical facility (office of hospital) for further clinical evaluation as described above with reference to FIG. 2A to determine whether a hydrocephalic condition has returned.

Once the patient returns to a non-hydrocephalic condition (i.e., ventricles normalize), the physician may identify through continued monitoring and recording the mean pressures and their minimum and maximum ranges indicative of the patient's daily circadian rhythm. According to certain embodiments, the main objective for the valve controller 360 is to keep the pressure gradient between Pcsf and Pp the same throughout the day as well as with variations associated with changes in the patient's body position (posture).

According to one embodiment, to initially program the adjustable valve 310 for a patient that has hydrocephalus, the physician may either use the pre-programmed default values or may select values based on prior history of the patient based on the previously measured pressure data and associated trends.

In certain embodiments, the method of obtaining the measurement of the intraparenchymal venous pressure (Pp) assumes that the intraparenchymal pressure (Pp) sensor 320 measures the higher of the intraparenchymal venous pressure (Pp) and the intraventricular CSF pressure (Pcsf). The Pp can track the Pcsf as the pressure setting of the adjustable valve 310 is reduced until the Pcsf drops below the Pp measurement. The measurement of the Pp may result in the treatment of hydrocephalus by reducing the Pcsf.

Figure 7:
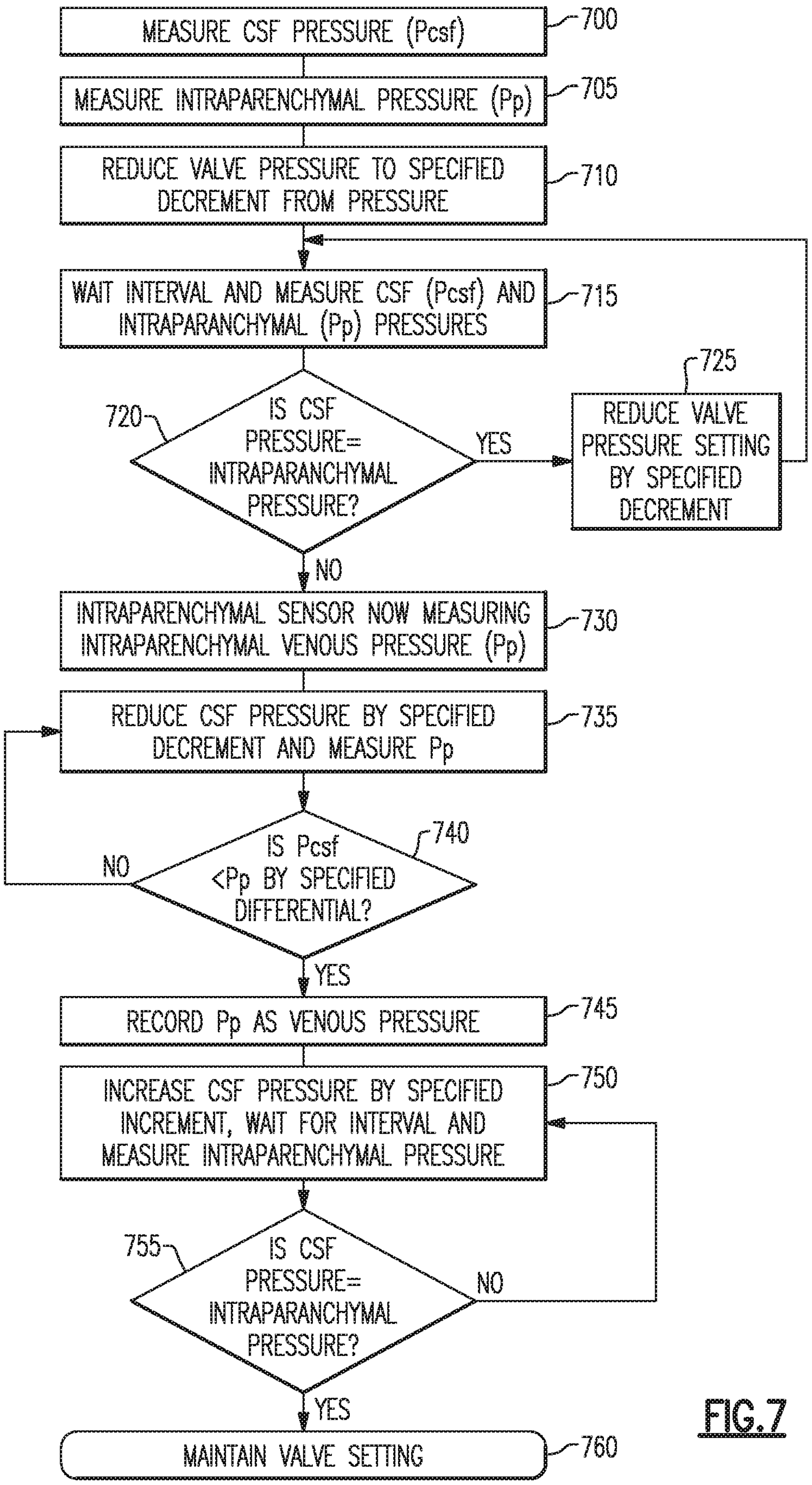
FIG. 7 is a flow chart of an example of the treatment algorithm during steady state operation.

An example of a control process is shown in FIG. 7. The control process may reside as firmware in the implanted valve controller 360. The process can include measuring the two pressures, which may be used in determining the differential pressure between the two compartments and, thus, the potential presence of a hydrocephalic condition. The measurement from the CSF pressure (Pcsf) sensor 330 and intraparenchymal pressure (Pp) sensor 320 may provide for the indirect measurement of the intraparenchymal venous pressure (Pp) in the determination of High Pressure Hydrocephalus (HPH).

As discussed above, pressure measurements may be taken with electronic pressure sensors, which may be mounted on the ventricular catheter 340, connected to the adjustable valve 310. Starting with step 700, the Pcsf may be measured and followed by the measurement of Pp in step 705 as baseline values. The algorithm residing in the valve controller 360 may reduce the valve pressure setting by a predetermined pressure (e.g., 10 mmH2O) in step 710. The adjusted valve pressure setting may be set by the physician or may be a preprogrammed default value. The valve controller 360 may then wait for a specified time interval (e.g., 1 hour) in step 715 for the pressures to stabilize and then may repeat the two measurements of the Pcsf and the Pp. The two pressure measurements may be compared in step 720 and if the Pcsf is equal to the Pp, the valve controller 360 may reduce the pressure setting of the adjustable valve 310 by a predetermined set pressure (e.g., 10 mmH2O), and may then wait for another specified time interval (e.g., 1 hour) to measure and assess the two pressures again. If the two pressures are not equal such that the Pcsf is lower than the Pp, the process may include identifying that the Pp value measured may be the true intraparenchymal venous pressure Pp in step 730. In steps 735 and 740, the process may include continuing to take the Pcsf and Pp measurements by reducing the valve pressure setting of the adjustable valve 310 until the difference between Pcsf and Pp is greater than a second a predetermined amount (e.g., 20 mmH2O) in step 740. Then, the valve controller 360 may record the Pp value in step 745. The process may include proceeding to increase the pressure setting of the adjustable valve 310 so that the Pcsf and the Pp may once again be within a specified equivalent range in step 750 indicative of a return to a normal state and may maintain the valve pressure setting in step 760.

Figure 8:
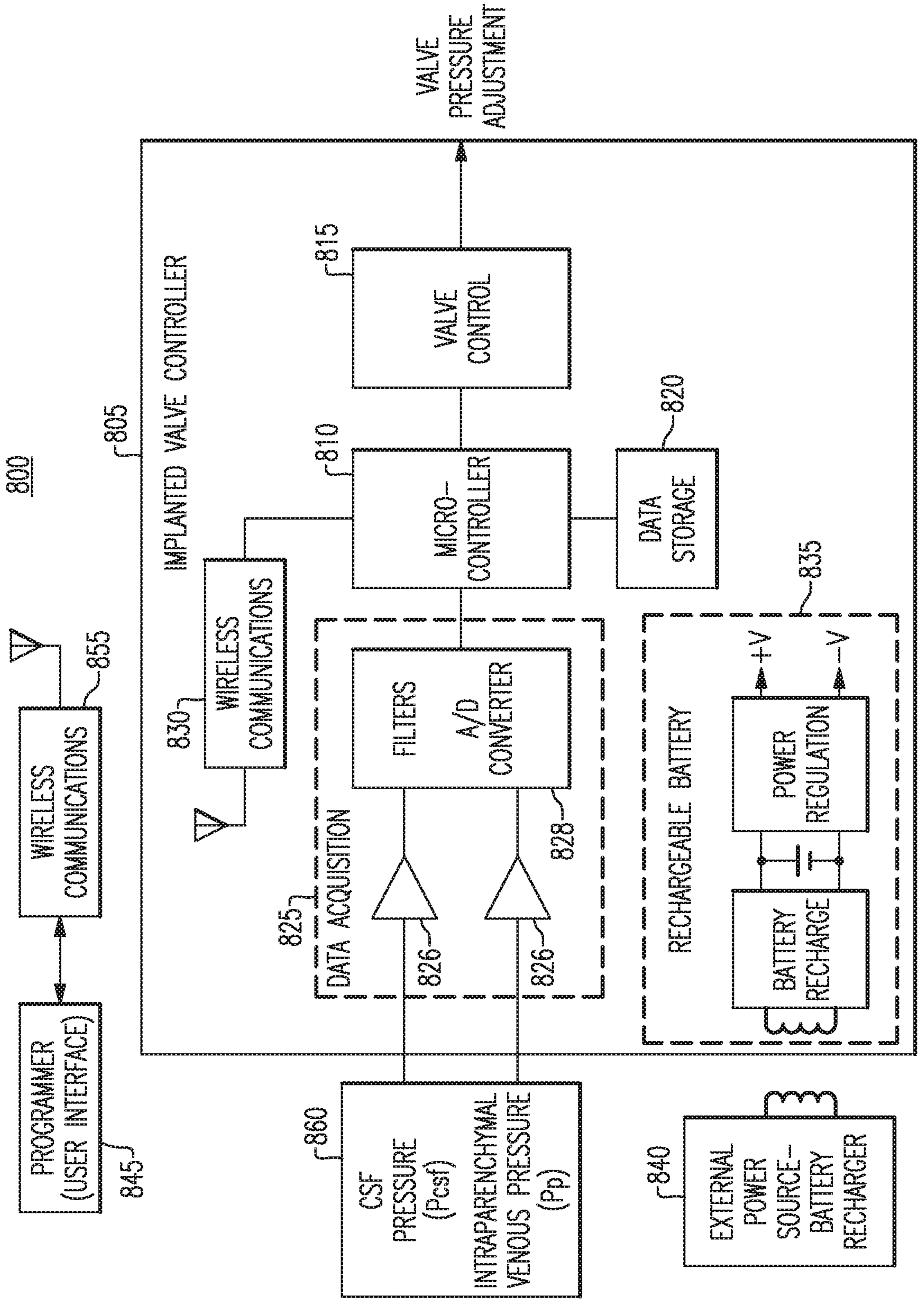
FIG. 8 is an electronic block diagram of an example of an implanted valve controller and external instrumentation.

FIG. 8 provides an electronic block diagram of an example of a self-adjusting valve system 800, including an implanted valve controller 805, and external instrumentation inclusive of a programmer 845 which may provide a user interface and an external wireless communications 855 module. For the example illustrated in FIG. 8, it is assumed that a small size for the implanted valve controller 805 may be desired, and therefore the implanted power source may be identified as a rechargeable battery 835 as is also shown in FIG. 5. The implanted rechargeable battery 835 may be recharged from a transcutaneous wireless power transfer method, known in the art, from an external power source-recharger 840. Wireless communications (855 and 830), between an external programmer 845 instrument and the implanted valve controller 805 may allow the physician the ability to review recorded pressure data and review the programmed settings for the implanted valve controller 805 and may provide the physician with the capability to adjust the operational settings of the implanted valve controller 805. The wireless communications (855 and 830), may be in the form of near field electromagnetic, or with a far field RF telemetry such as MICS (Medical Implant Communication Services) method, both of which are known in the art.

The implanted valve controller 805 may include a data acquisition module 825 for recording pressures such as the Pcsf and the Pp pressures 860. The data acquisition module 825 may include circuits such as amplifiers 826, filters and analog-to-digital (A/D) converter(s) 828. The signals from the data acquisition module 825 may be interpreted by a microcontroller 810 which may perform firmware algorithms to implement the processes as described in the flowcharts of FIG. 6 and FIG. 7. The implanted valve controller 805 may further include data storage 820, such as flash memory, which may contain the operational firmware (e.g., algorithms) and may also store measured data and/or recorded physiological data. The microcontroller 810 may also interface with a valve control circuit 815, which may send signals to the hydrocephalus valve within the implanted self-adjusting valve/controller 560 device as per FIG. 5 for changing the pressure setting of the self-adjusting valve/controller 560 device. In addition, prior to intentionally exposing the valve to a strong magnetic field such as imaging the patient using magnetic resonance imaging (MRI), the programmer 845 may be used to retrieve data from the implanted valve controller 805 to allow the physician to review the programmed operating pressure of the self-adjusting valve/controller 560 device. After imaging with MRI, the programmer 845 may be used again to retrieve data from the implanted valve controller 805 and may automatically reprogram the implanted valve controller 805 to the pre-MRI operating pressure setting. Furthermore, the programmer 845 may also store the last programmed settings of the implanted valve controller 805 which may be used to restore the operating pressure of the implanted valve controller 805 to that programmed setting in situations of accidental adjustment when exposed to a strong magnetic field may be suspected.

Although certain examples may use an implanted self-adjusting valve and optionally an implanted valve controller, as discussed above, in other examples the self-adjusting valve and the valve controller may remain external to the patient. For example, as discussed above, the self-adjusting valve can be connected to an implanted ventricular or lumbar catheter that may be part of an external ventricular drainage system. Thus, the self-adjusting valve can be configured to drain CSF to a location internal to the patient's body or to an external device, such as a bag or other fluid container connected to the ventricular drainage catheter. The outputs of the sensors (Pcsf and/or intraparenchymal pressure (Pp) sensors) may be output a display screen directly or processed using algorithms to display physiological parameters to facilitate clinical assessment of the patient.

Figure 9A:
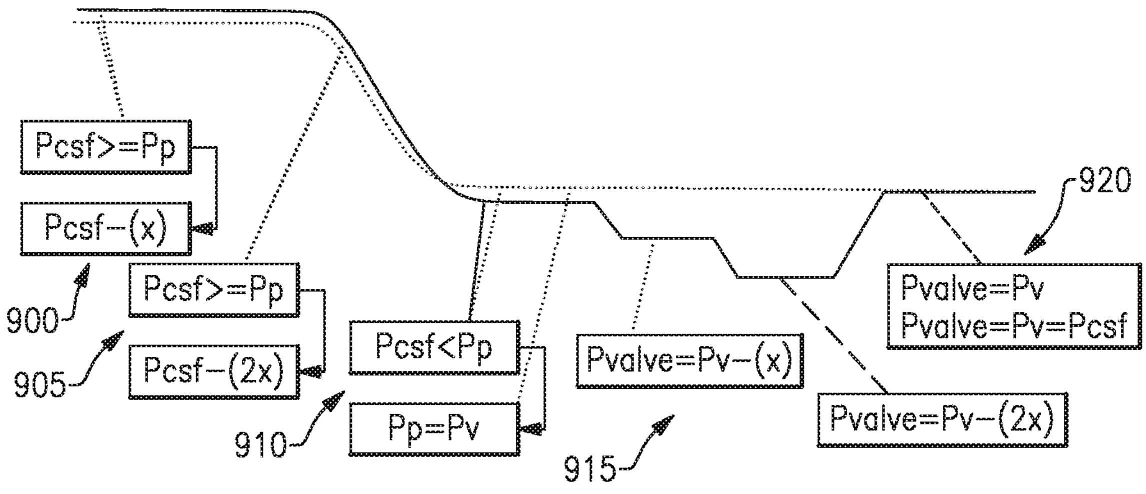
FIG. 9A is a graph illustrating a time-based graphical representation of the pressure measurements for the algorithm of the flow chart presented in FIG. 6.

FIG. 9A illustrates a time-based graphical representation of an example of the process illustrated in FIG. 7 for a set of suitable pressure readings from a hydrocephalus patient treated with a self-adjusting valve. In the first phase 900, the Pp measured value may track the Pcsf measurement such that Pcsf may be greater than or equal to Pp. In the second phase 905, Pp measurement may continue to track Pcsf measurement while the pressure setting of the valve is reduced. Once the Pcsf measurement drops below the measured value of Pp as in step 910, it may be assumed that the measured value of Pp may be indicative of the true intraparenchymal venous pressure (Pp). In the third phase 915, the valve pressure setting may continue to be decreased until the Pcsf represents the desired pressure to reduce the hydrocephalic condition. In step 920 the pressure setting of the adjustable valve 310 may then be increased until Pcsf and Pp are once again equal, returning to steady state and reaching an equilibrium of intracranial pressures while maintaining a normal ventricular volume.

Figure 9B:
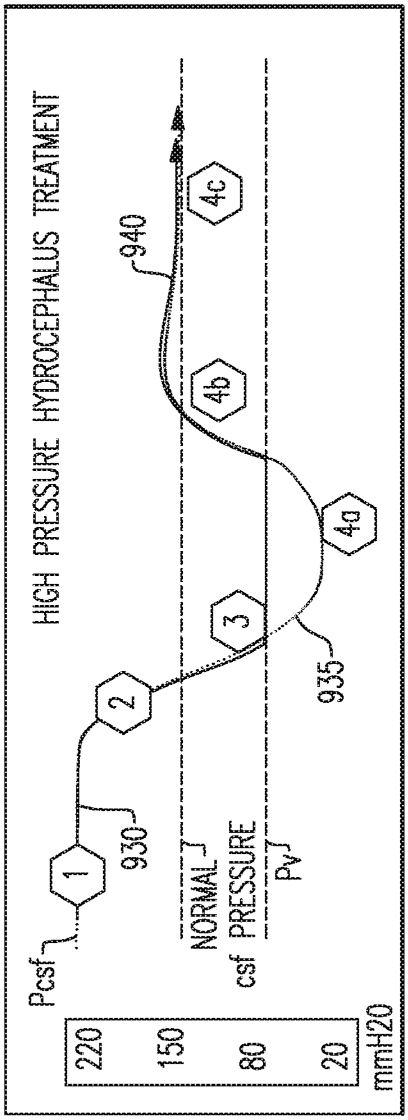
FIG. 9B is a graph illustrating the steps followed in an example of the treatment of High Pressure Hydrocephalus.
Figure 9C:
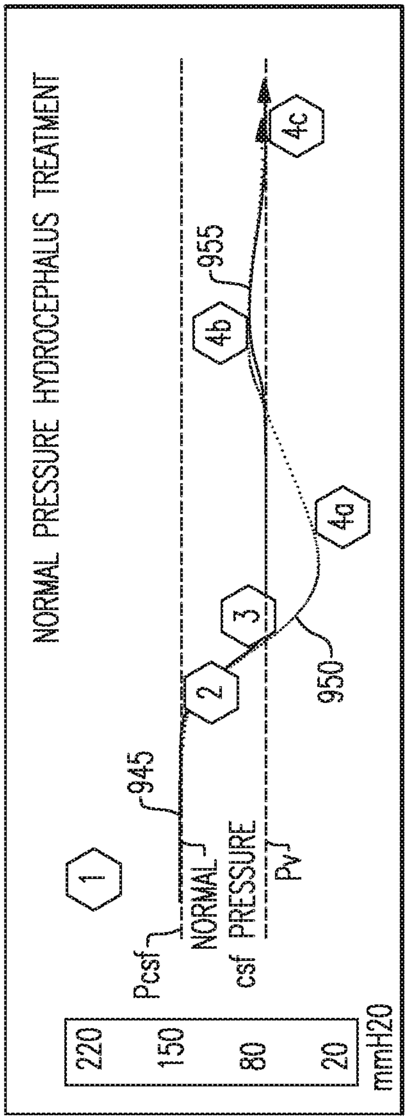
FIG. 9C is a graph illustrating the steps followed in an example of the treatment of Normal Pressure Hydrocephalus.

FIG. 9B and FIG. 9C illustrate the steps that may be followed in the treatment of HPH and respectively NPH. As discussed above, a principle of operation behind the self-adjusting valve is that the gradient between the Pcsf and Pp is what controls ventricular volume. By measuring these two parameters and adjusting the Pcsf up or down with respect to Pp, the adjustable valve 310 may control ventricular volume by controlling the gradient between these two pressures.

In a first example as shown in FIG. 9B, the Pcsf may be initially measured at 220 mm H2O along with a measured Pp tracking at the same value as both sensors track at the highest measured pressure value 930 in step 1. Even though Pcsf may be greater than Pp, both sensors may measure the higher of the two actual pressures. The desired normal Pcsf may be equal to Pp. By slowly reducing the pressure setting of the adjustable valve 310 in step 2, which may reduce Pcsf value, the Pp measurement may continue to track the Pcsf. Once the Pcsf and Pp both reach the true Pv of 80 mm H2O at step 3 (which represents the pressure of the superior sagittal sinus (SSS)), the Pp measured value may not reduce any further but additional reduction in Pcsf may allow the ventricles to drain CSF 935, and may reduce the ventricular volume occurring in step 4*a*. After a specified interval (e.g., 1 hour), which may allow the ventricles to reach a normal volume, the valve pressure setting may then be increased until the Pcsf and Pp are once again equal, and Pcsf is slightly higher than the target Pp (step 4*b*). A steady state condition may then be maintained 940 with Pcsf equal to Pp and Pv (step 4*c*), by reaching an equilibrium of intracranial pressures and maintaining a normal ventricular volume.

In a second example as illustrated in FIG. 9C, Pcsf may be initially measured at a normal value of 150 mm H2O with Pp tracking the Pcsf value. The actual Pp value may be lower at 80 mmH2O resulting in NPH. As with HPH in step 1, the measured Pp may track Pcsf at the same value since both sensors track at the highest measured pressure value 945. By slowly reducing the valve pressure setting in step 2 which may reduce Pcsf, the Pp measurement may also continue to track the Pcsf. Once the Pcsf and Pp pressures reach the true Pv of 80 mm H2O at step 3, Pp may not be reduced any further but additional reduction in Pcsf which may allow the ventricles to drain CSF 950, and may reduce the ventricular volume as shown in step 4*a*. After a specified interval (e.g., 1 hour), the valve pressure setting may then be increased until the Pcsf and Pp are once again equal, and Pcsf is slightly higher than the target Pp (step 4*b*). A steady state condition may then be maintained 955 with Pcsf equal to Pp and Pv (step 4*c*), by reaching an equilibrium of intracranial pressures and maintaining a normal ventricular volume.

With both examples of FIG. 9B and FIG. 9C, the differential pressure between Pcsf and Pp is a main factor for reducing the ventricular volume conditions associated with hydrocephalus.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. It is to be appreciated that embodiments of the methods and apparatuses discussed herein are not limited in application to the details of construction and the arrangement of components set forth in the above description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Accordingly, the foregoing description and drawings are by way of example only, and the scope of the invention should be determined from proper construction of the appended claims, and their equivalents.

What is claimed is:

1. A method of accurately measuring a pressure within a human brain, the method comprising:

providing a valve controller operably connected to a shunt valve assembly configured to vent fluid from a ventricle of the brain to an outlet port;

measuring a cerebrospinal fluid pressure (Pcsf) within the ventricle of the brain with a first pressure sensor operably connected to the valve controller;

measuring a second measured pressure (Pp) within a parenchyma space of the brain with a second pressure sensor operably connected to the valve controller; and with the valve controller, calculating an effective differential pressure (Pei=Pcsf−Pp) between the measured Pcsf and the measured Pp;

wherein the valve controller is programmed to determine whether the effective differential pressure has exceeded a predetermined level associated with a condition of hydrocephalus;

reduce, responsive to determining that the effective differential pressure is less than the predetermined level, a pressure setting of the shunt valve assembly until the measured Pcsf is lower than the measured Pp by a specified differential pressure threshold; and identify, responsive to determining that the effective differential pressure is greater than the predetermined level, the measured Pp as being indicative of a true Pp, wherein the true Pp is an accurate measurement of intraparenchymal venous pressure within the human brain.

2. The method of claim 1, wherein the reduction of the cerebrospinal fluid pressure treats at least one of High Pressure Hydrocephalus, Normal Pressure Hydrocephalus or other types of dementia, or the condition of Pseudotumor cerebri (Idiopathic Intracranial Hypertension) or the like.

3. The method of claim 1, wherein continued measurements of the Pcsf and the Pp provide a steady state balance of ventricular volume and the intraparenchymal venous pressure.

4. A method of operating a surgically-implantable shunt valve with pressure sensors configured to be implantable in fluid communication with a ventricle of a brain of a patient, the method comprising:

providing a valve controller operably connected to the shunt valve;

operably connecting the valve controller to a first pressure sensor and a second pressure sensor configured to provide pressure data to the valve controller;

measuring a cerebrospinal fluid pressure (Pcsf) within the ventricle of the brain with the first pressure sensor;

measuring a secondary pressure (Pp) within a parenchyma space of the brain with the second pressure sensor;

with the valve controller, calculating a differential pressure between the measured Pcsf and the measured Pp; and determining whether to adjust a pressure setting of the shunt valve based on the differential pressure, wherein the valve controller is programmed to determine whether the differential pressure between the measured Pcsf and the measured Pp has exceeded a predetermined level associated with a condition of hydrocephalus;

reduce, responsive to determining that the differential pressure between the measured Pcsf and the measured Pp is less than the predetermined level, a pressure setting of the shunt valve by a predetermined value; and identify, responsive to determining that the differential pressure between the measured Pcsf and the measured Pp is greater than the predetermined level, the measured Pp as being indicative of a true Pp, wherein the Pcsf being greater than a first predetermined threshold is indicative of High Pressure Hydrocephalus, and the Pcsf being normal is indicative of Normal Pressure Hydrocephalus.

5. The method of claim 4, wherein the valve controller is programmed to continue reducing the pressure setting of the shunt valve until the differential pressure is greater than a second predetermined level.

6. The method of claim 5, wherein the valve controller is programmed to maintain the pressure setting until the ventricle returns to normal size or volume.

7. The method of claim 6, wherein the valve controller is programmed to increase the pressure setting of the shunt valve until the measured Pp and the measured Pcsf are equal.

8. The method of claim 7, further comprising recording values of the measured Pp and the measured Pcsf in memory using the valve controller.

9. The method of claim 4, further comprising using the valve controller to reduce the pressure setting of the shunt valve by a predetermined decrement.

10. The method of claim 9, wherein the valve controller is programmed to continue to reduce the pressure setting of the shunt valve until the differential pressure between the measured Pp and the measured Pcsf is greater than a second predetermined level.

11. The method of claim 10, wherein the valve controller is programmed to maintain the pressure setting until the ventricle returns to normal size or volume and optionally increase the pressure setting of the shunt valve until the measured Pp and the measured Pcsf are equal.

12. The method of claim 11, further comprising recording the measured Pp and the measured Pcsf values in memory using the valve controller.

13. A method of operating a with pressure sensors configured to be in fluid communication with a ventricle of a brain, the method comprising:

providing a valve controller operably connected to the shunt valve, a first pressure sensor, and a second pressure sensor;

measuring a cerebrospinal fluid pressure (Pcsf) within a ventricle of a brain with the first pressure sensor;

measuring a secondary pressure (Pp) within a parenchyma space of the brain with the second pressure sensor;

with the valve controller, calculating a differential pressure between the measured Pcsf and the measured Pp; and with the valve controller, determining whether to adjust a pressure setting of the shunt valve based on the differential pressure, wherein the valve controller is programmed to determine whether the differential pressure between the measured Pcsf and the measured Pp has exceeded a predetermined level associated with a condition of hydrocephalus;

reduce, responsive to determining that the differential pressure between the measured Pcsf and the measured Pp is less than a predetermined level, the pressure setting of the shunt valve by a predetermined value; and identify, responsive to determining that the differential pressure between the measured Pcsf and the measured Pp is greater than the predetermined level, the measured Pp as being indicative of a true Pp; and wherein the valve controller is further programmed to record values of the measured Pp and the measured Pcsf in memory.

14. A shunt valve system, comprising:

a shunt valve assembly configured to vent fluid from a ventricle of the brain to an outlet port;

a valve controller operably connected to the shunt valve assembly;

a first pressure sensor operably connected to the valve controller, the first pressure sensor configured to measure a cerebrospinal fluid pressure (Pcsf) within the ventricle of the brain; and a second pressure sensor operably connected to the valve controller, the second pressure sensor configured to measure a second measured pressure (Pp) within a parenchyma space of the brain;

wherein the valve controller is programmed to:

calculate an effective differential pressure (Pei=Pcsf−Pp) between the measured Pcsf and the measured Pp;

determine whether the effective differential pressure has exceeded a predetermined level associated with a condition of hydrocephalus;

reduce, responsive to determining that the effective differential pressure is less than the predetermined level, a pressure setting of the shunt valve assembly by a predetermined value until the measured Pcsf is lower than the measured Pp by a specified differential pressure threshold; and identify, responsive to determining that the effective differential pressure is greater than the predetermined level, the measured Pp as being indicative of a true Pp, wherein the true Pp is an accurate measurement of intraparenchymal venous pressure within the human brain.

15. The shunt valve system of claim 14, wherein the valve controller is further programmed to record values of the measured Pp and the measured Pcsf in memory.

16. The shunt valve system of claim 15, wherein the valve controller is-programmed to continue reducing the pressure setting of the shunt valve assembly until the differential pressure is greater than a second predetermined level.

17. The shunt valve system of claim 16, wherein the valve controller is programmed to maintain the pressure setting until the ventricle returns to normal size or volume.

18. The shunt valve system of claim 17, wherein the valve controller is programmed to increase the pressure setting of the shunt valve assembly until the measured Pp and the measured Pcsf are equal.

19. The shunt valve system of claim 14, wherein the shunt valve assembly is configured to be surgically implantable.

20. The shunt valve system of claim 14, wherein the shunt valve assembly is configured to be external.

21. The shunt valve system of claim 14, wherein the valve controller is configured to be surgically implantable.

* * * * *